US007560235B2

(12) United States Patent
Kobayashi

(10) Patent No.: US 7,560,235 B2
(45) Date of Patent: Jul. 14, 2009

(54) METHOD OF DETECTING REACTION OF DNA AND DNA-BINDING PROTEIN

(75) Inventor: Tamiyo Kobayashi, Kunitachi (JP)

(73) Assignee: Olympus Corporation, Tokyo (JP)

( * ) Notice: Subject to any disclaimer, the term of this patent is extended or adjusted under 35 U.S.C. 154(b) by 315 days.

(21) Appl. No.: 11/311,827

(22) Filed: Dec. 19, 2005

(65) Prior Publication Data

US 2006/0166237 A1 Jul. 27, 2006

Related U.S. Application Data

(63) Continuation of application No. PCT/JP2004/008857, filed on Jun. 17, 2004.

(30) Foreign Application Priority Data

Jun. 19, 2003 (JP) ............................ 2003-175186

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 5,804,374 | A | * | 9/1998 | Baltimore et al. | ............... | 435/6 |
| 5,815,262 | A | * | 9/1998 | Schrof et al. | ................. | 356/318 |
| 5,840,503 | A | * | 11/1998 | Beausang et al. | ........... | 435/7.21 |

FOREIGN PATENT DOCUMENTS

WO  WO 03/018836 A2  3/2003

OTHER PUBLICATIONS

Sevenich et al. ("DNA binding and oligomerization of NtrC studied by fluorescence anisotropy and fluorescence correlation spectroscopy" Nucleic Acids Res. Mar. 15, 1998;26(6):1373-81).*
Reiker et al. "Isolation of the nitrogen assimilation regulator NR(I), the product of the glnG gene of *Escherichia coli*" Proc Natl Acad Sci U S A. Sep. 1983;80(18):5554-5558.*
Sevenich, F. W., et al., "DNA binding and oligomerization of NtrC studied by fluorescence anisotropy and fluorescence correlation spectroscopy", Nucleic Acids Research, 1998, vol. 26, No. 6, pp. 1373-1381.

Sterrer, S., et al., Fluorescence Correlation Spectroscopy (FCS)—A Highly Sensitive Method to Analyze Drug/Target Interactions, Journal of Receptor & Signal Transduction Research, 17(1-3), pp. 511-520, 1997.
H O and Tumor Necrosis Factor- Induce Differential Binding of The Redox-responsive Transcription Factors AP-1 and NF- B to the Interleuken-8 Promoter In Endothelial and Epithelial Cells, The Journal of Biological Chemistry, vol. 273, pp. 32670-32678, Dec. 4, 1998.
Xie, Qiao-wen, et al., "Role of Transcription Factor NF- B/Rel in Induction of Nitric Oxide Synthase", The Journal of Biological Chemistry, vol. 269, pp. 4705-4708, Feb. 18, 1994.
Yakovleva T. et al., "p53 Latency-Out of the Blind Alley", *Trends in Biochemical Sciences* 27(12):612-618 (2002), XP-004395941.
Földes-Papp Z. et al., "A New Dimension for the Development of Fluorescence-Based Assays in Solution: From Physical Principles of FCS Detection to Biological Applications", *Experimental Biology and Medicine* 227(5):291-300 (2002), XP-002403399.
Haustein E. et al., "Ultrasensitive Investigations of Biological Systems by Fluorescence Correlation Spectroscopy", *Methods* 29(2):153-166 (2003), XP-002403400.
Craenenbroeck E.V. et al., "Fluorescence Correlation Spectroscopy: Molecular Recognition at the Single Molecule Level", *Journal of Molecular Recognition* 13(2):93-100 (2000), XP-008002275.
Kobayashi T. et al., "Detection of Protein-DNA Interactions in Crude Cellular Extracts by Fluorescence Correlation Spectroscopy", *Analytical Biochemistry* 332(1):58-66 (2004), XP-004525465.
Kinjo, M., "Tanpakushitsu Kakusan Koso No. 1 Bunshi Sokutei to Sosaho Keiko Sokan Bunkoho ni Yoru 1 Bunshi Kenshutsu, Protein Nucleic acid and Enzyme". 1999, vol. 44, No. 9, pp. 1431-1438 (English translation).

* cited by examiner

*Primary Examiner*—Kenneth R. Horlick
*Assistant Examiner*—Christopher M. Babic
(74) *Attorney, Agent, or Firm*—Scully, Scott, Murphy & Presser, P.C.

(57) ABSTRACT

In the case of detecting whether or not a binding site of a transcription factor TFIID and a transcription factor TFIIB is present in a labeled DNA, the presence of a binding site can be detected precisely by adding all of a transcription factor TFIID, a transcription factor TFIIB and an anti-TFIIB antibody to a DNA-containing solution, and obtaining a translational diffusion time of the binding product by FCS-measurement. Information for obtaining a translational diffusion time is obtained, by mixing the sample and measuring it by fluorescence correlation spectroscopy (FCS), and as a result, detection result can be simply obtained in a short time, without performing troublesome operation such as utilization of a radioisotope and selection by an electrophoresis method or immobilization of a molecule on a solid substrate.

4 Claims, 17 Drawing Sheets

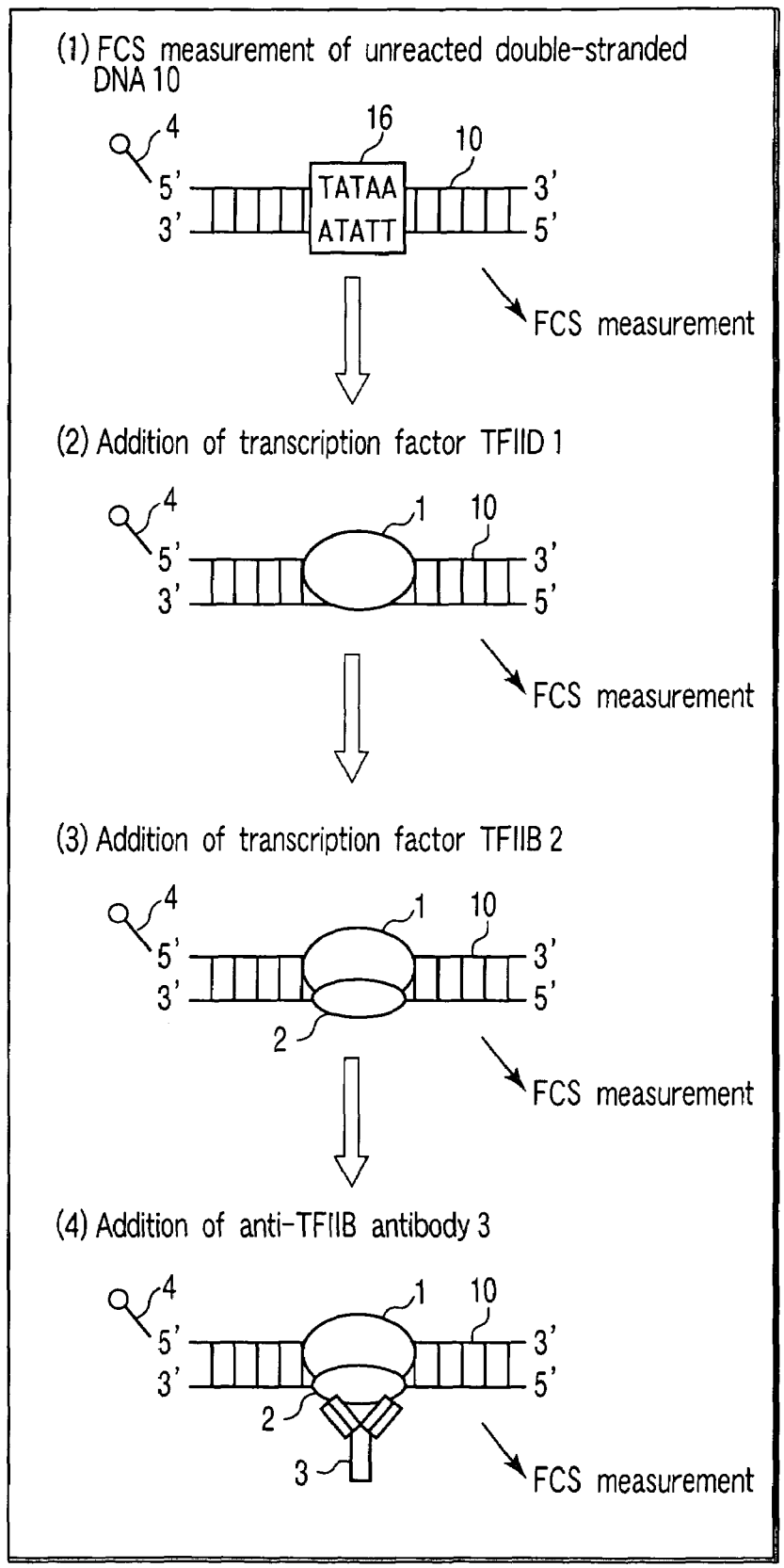
F I G. 1

(1) FCS measurement of unreacted double-stranded DNA 20

(2) Addition of transcription factor AP-1 5

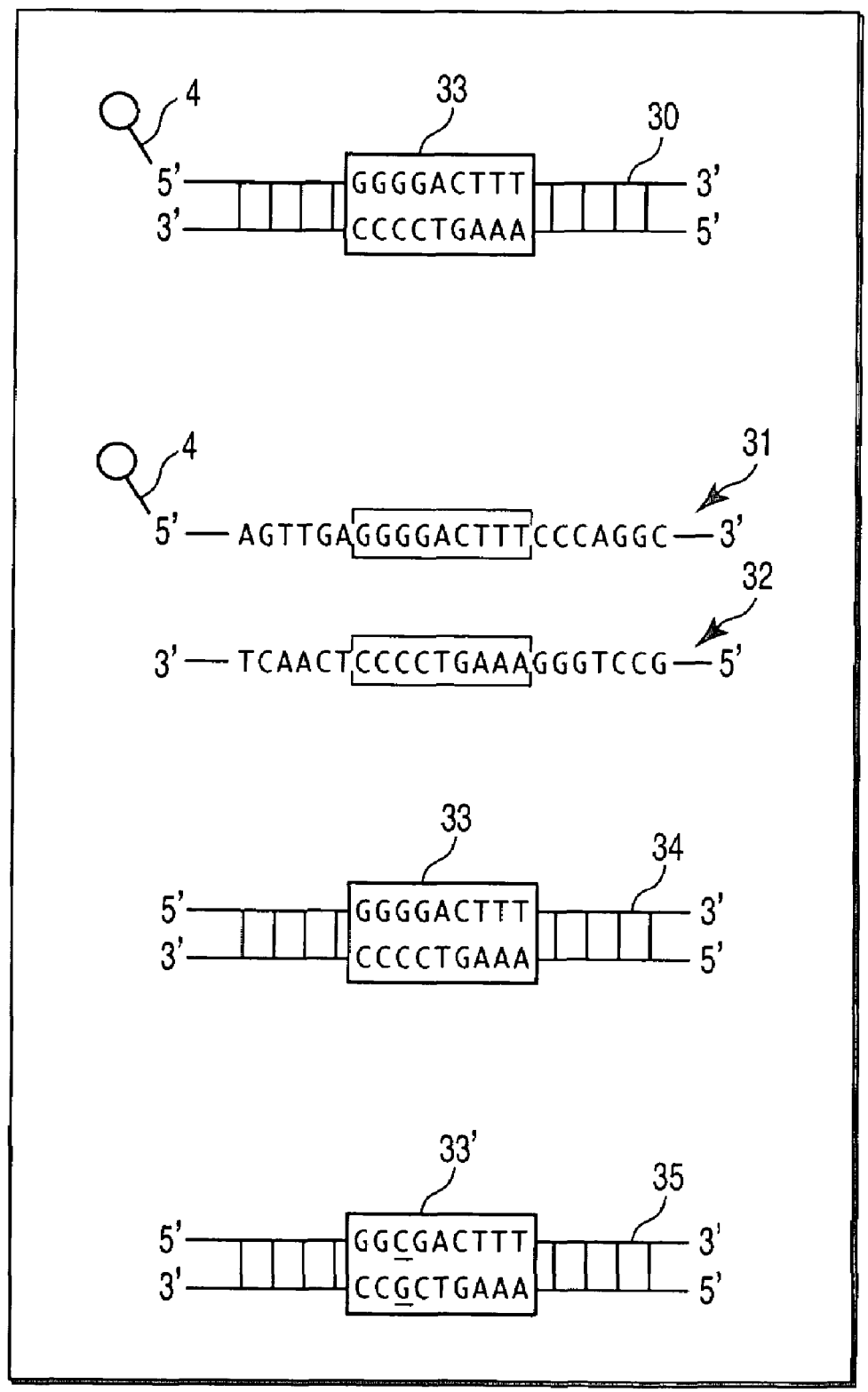
F I G. 7

(1) Double-stranded DNA before reaction
(2) Addition of transcription factor TFIID 1
(3) Addition of transcription factor TFIID 1 and transcription factor TFIIB 2
(4) Addition of transcription factor TFIID 1, transcription factor TFIIB 2 and anti-TFIIB antibody 3

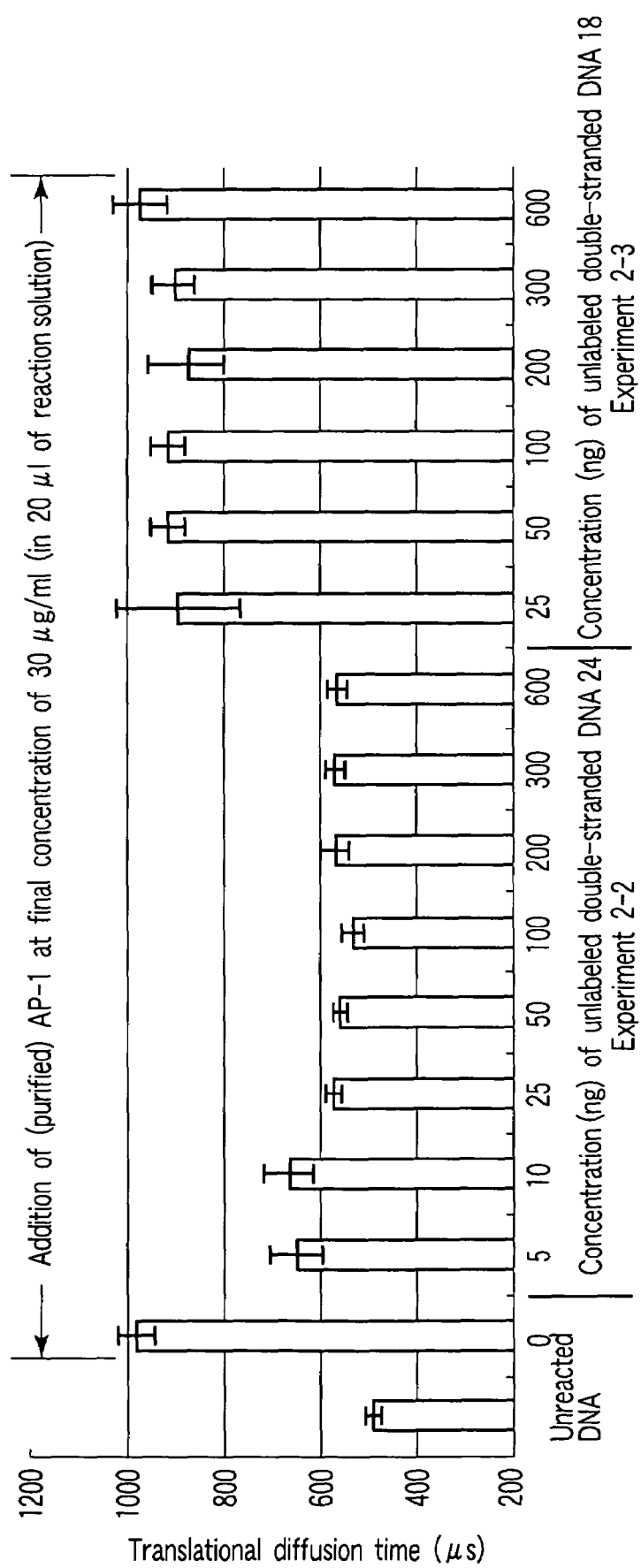
F I G. 11

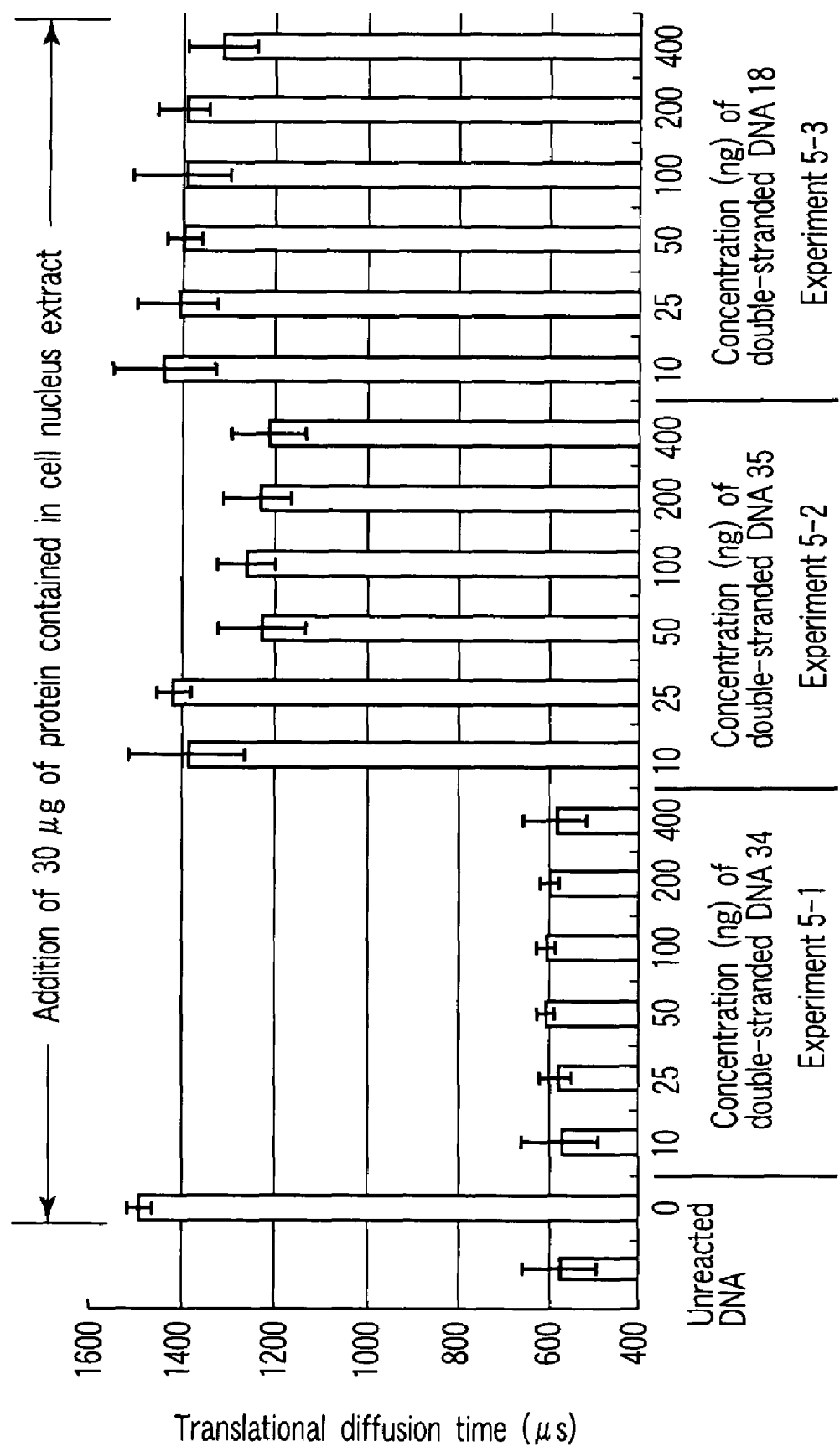
F I G. 17

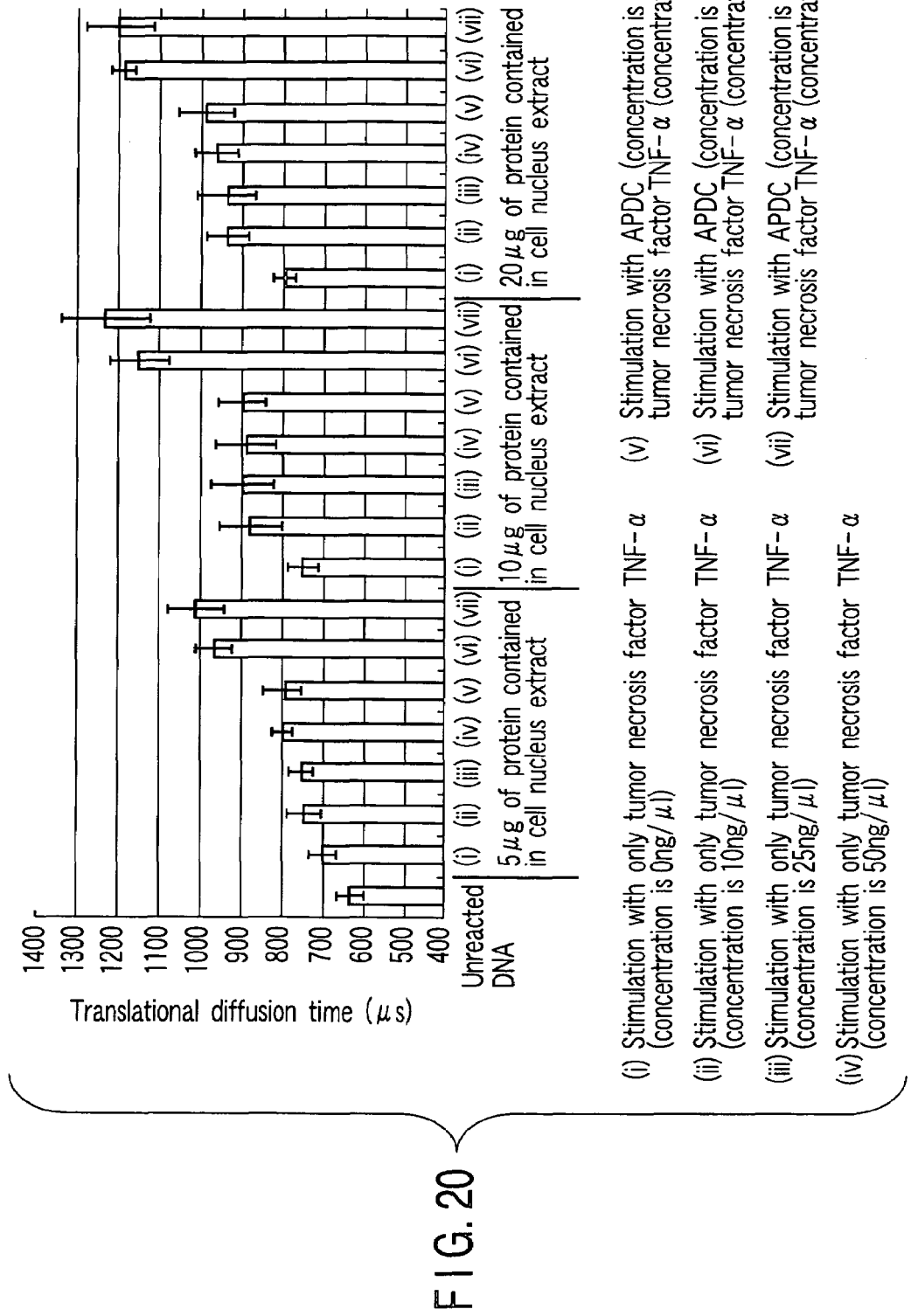

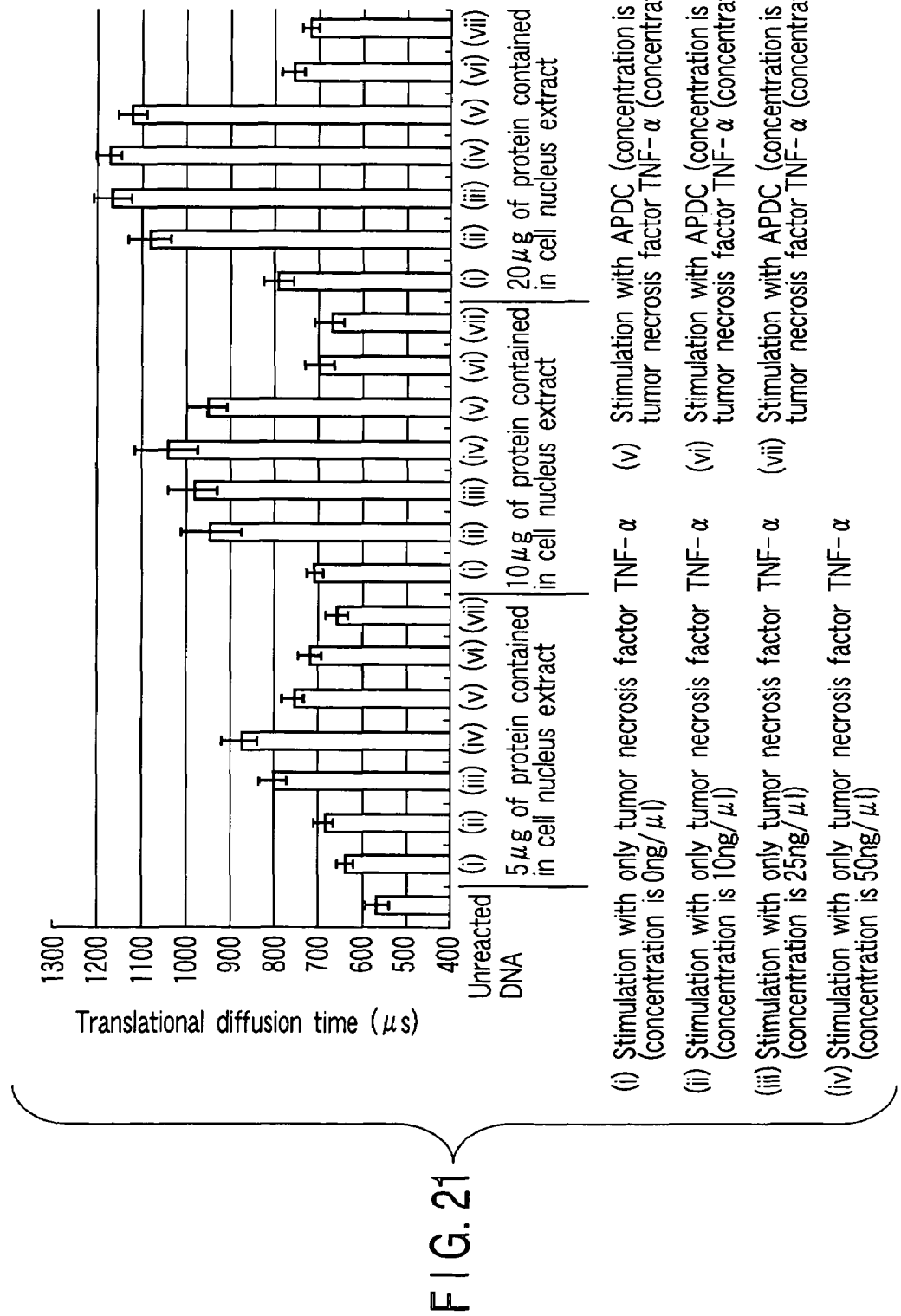

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: DNA having
      no binding site for transcription factor AP-1

<400> SEQUENCE: 1
caggcgcgtt ttgaccatct t                                          21
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: DNA having
      no binding site for transcription factor AP-1

<400> SEQUENCE: 2
aagatggtca aaacgcgcct g                                            21

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: DNA having
      a binding site for transcription factor TFIID

<400> SEQUENCE: 3
gcagagcata taaggtgagg tagga                                        25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: DNA having
      a binding site for transcription factor TFIID

<400> SEQUENCE: 4
tcctacctca ccttatatgc tctgc                                        25

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: DNA having
      a binding site for transcription factor AP-1

<400> SEQUENCE: 5
gcgttgatga gtcagccgga a                                            21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: DNA having
      a binding site for transcription factor AP-1

<400> SEQUENCE: 6
ttccgcgtga ctcatcaacg c                                            21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: DNA having
      a binding site for transcription factor NF-kB

<400> SEQUENCE: 7
agttgagggg actttcccag gc                                           22

```
<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: DNA having
      a binding site for transcription factor NF-kB

<400> SEQUENCE: 8
gcctgggaaa gtcccctcaa ct                                              22
```

METHOD OF DETECTING REACTION OF DNA AND DNA-BINDING PROTEIN

CROSS REFERENCE TO RELATED APPLICATIONS

This is a Continuation Application of PCT Application No. PCT/JP2004/008857, filed Jun. 17, 2004, which was published under PCT Article 21(2) in Japanese.

This application is based upon and claims the benefit of priority from prior Japanese Patent Application No. 2003-175186, filed Jun. 19, 2003, the entire contents of which are incorporated herein by reference.

BACKGROUND OF THE INVENTION

1. Field of the Invention

The present invention relates to a method of detecting a reaction of a DNA and a DNA-binding protein, more particularly, a method of detecting the reaction using fluorescence correlation spectroscopy (FCS).

2. Description of the Related Art

Patent Publication 1 (Japanese Patent No. 3169610) describes a method of screening a molecule which can bind to a test sequence selected in a double-stranded DNA.

Patent Publication 2 (Japanese Patent No. 2953783) describes an effective method of identifying a drug which is active at a gene transcription level.

Patent Publication 3 (Jpn. Pat. Appln. KOKAI Publication No. 2001-321199) describes a method of quantitating a DNA-binding protein in a biological sample.

Patent Publication 4 (Jpn. Pat. Appln. KOKAI Publication No. 2003-88369) describes a method of detecting DNA endonuclease activity utilizing fluorescence correlation spectroscopy (FCS), and a relationship between a size of a molecular weight and a length of a translational diffusion time.

Patent Publication 5 (Jpn. Pat. Appln. KOKAI Publication No. 2002-543414) describes a method of characterizing a fluorescent molecule or other particle in a sample, and describes that a translational diffusion time is obtained from fluorescence intensity multiple distribution analysis (FIMDA) and fluorescence autoconvoluted intensity distribution analysis (FACID).

Among the aforementioned prior art, the detecting methods described in Patent Publication 2 (Japanese Patent No. 2953783), Patent Publication 3 (Jpn. Pat. Appln. KOKAI Publication No. 2001-321199) and Patent Publication 4 (Jpn. Pat. Appln. KOKAI Publication No. 2003-88369) use a radioisotope, or perform selection by an electrophoresis method or immobilization of a molecule on a solid substrate, when a particular sequence or a molecule having a particular sequence is detected, and therefore there is a problem that operation is troublesome and it takes a time for obtaining detection results.

Patent Publication 4 (Jpn. Pat. Appln. KOKAI Publication No. 2003-88369) and Patent Publication 5 (Jpn. Pat. Appln. KOKAI Publication No. 2002-543414) do not describe a method of detecting a reaction of a DNA and a DNA-binding protein.

BRIEF SUMMARY OF THE INVENTION

An object of the present invention is to provide a method of detecting a reaction of a DNA and a DNA-binding protein simply and in a short time.

A feature of the present invention which attains the aforementioned object is to mix a solution containing a fluorescently labeled double-stranded DNA with a transcription factor TFIID, and to obtain a translational diffusion time of a substance having a fluorescent label in the mixed solution by fluorescence correlation spectroscopy. According to the present invention, information for obtaining a translational diffusion time is obtained by mixing a solution and measuring by fluorescence correlation spectroscopy. Therefore, according to the present invention, a reaction of a double-stranded DNA and a transcription factor TFIID which is a DNA-binding protein can be simply detected in a short time, without performing troublesome operation such as utilization of a radioisotope and selection by an electrophoresis method or immobilization of a molecule on a solid substrate.

In addition, when each experiment is performed using a solution having a double-stranded DNA concentration in a sample of 2 nM to 5 nM, the particle number in a confocal volume becomes 2 to 5 at the time of FCS measurement. As a result, FCS measurement can be performed precisely, and thereby a binding reaction between a double-stranded DNA and a DNA-binding protein can be detected precisely. In particular, even when the particle number in a confocal volume is 2 to 3, precise detection is possible. Therefore, the detection method of the present invention is suitable also when a large amount of a double-stranded DNA or a DNA-binding protein can not be prepared, or when detection result is desired with only a small amount of a sample.

(2) Another feature of the present invention is to mix a solution containing a fluorescently labeled double-stranded DNA, a transcription factor TFIID and a transcription factor TFIIB, and to obtain a translational diffusion time of a substance having a fluorescent label in the mixed solution by fluorescence correlation spectroscopy. In this case, a translational diffusion time of a reaction product is extended by adding a transcription factor TFIIB, and therefore the binding can be detected more precisely. In addition, when an anti-TFIIB antibody is further added to the mixed solution, a translational diffusion time of a reaction product is further extended, and therefore the binding can be detected more precisely.

In the case of detecting whether or not a transcription factor TFIID-binding sequence is contained in a double-stranded DNA, a fluorescent label is attached to a double-stranded DNA, and any method of claims 1 to 3 is performed. If binding is detected, this results in that a transcription factor TFIID-binding sequence is contained in a double-stranded DNA.

In the case of detecting whether or not a transcription factor TFIID is contained in a test solution, the test solution and a fluorescently labeled double-stranded DNA having a transcription factor TFIID-binding sequence are mixed, and a translational diffusion time of a substance having a fluorescent label in the mixed solution is obtained by fluorescence correlation spectroscopy. In this case, the presence of a transcription factor TFIID can be detected more precisely, by adding either a transcription factor TFIIB, or adding a transcription factor TFIIB and an anti-TFIIB antibody.

Another feature of the present invention is to mix a solution to be detected with a solution containing a fluorescently labeled double-stranded DNA having a transcription factor AP-1-binding sequence, and to obtain a translational diffusion time of a substance having a fluorescent label in a mixed solution by fluorescence correlation spectroscopy. According to this feature, information for obtaining a translational diffusion time is obtained by mixing a solution and measuring by fluorescence correlation spectroscopy. Therefore, according to this feature, a reaction of a double-stranded DNA and a transcription factor AP-1 which is a DNA-binding protein can be simply detected in a short time, without performing troublesome operation such as utilization of a radioisotope and selection by an electrophoresis method or immobilization of a molecule on a solid substrate.

Another feature of the present invention is to mix a solution containing a double-stranded DNA to be detected, a transcription factor AP-1, and a fluorescently labeled double-stranded DNA having a transcription factor AP-1-binding sequence, and to obtain a translational diffusion time of a substance having a fluorescent label in a mixed solution by fluorescence correlation spectroscopy.

According to this feature, information for obtaining a translational diffusion time is obtained by mixing a solution and measuring by fluorescence correlation spectroscopy. Therefore, according to this feature, a reaction of a double-stranded DNA and a transcription factor AP-1 which is a DNA-binding protein can be simply detected in a short time, without performing troublesome operation such as utilization of a radioisotope and selection by an electrophoresis method or immobilization of a molecule on a solid substrate.

Another feature of the present invention is to stepwise increase an amount of a solution to be detected, when the solution to be detected is mixed with a fluorescently labeled double-stranded DNA having a transcription factor-binding sequence, and to obtain a translational diffusion time of a substance having a fluorescent label in the mixed solution by fluorescence correlation spectroscopy at each stage. In the case where a transcription factor AP-1 is detected in a cell nucleus extract, a double-stranded DNA having a transcription factor AP-1-binding site is used as a fluorescently labeled double-stranded DNA, and an amount of a cell nucleus extract solution is increased stepwise. In the case where a transcription factor NF-κB is detected in a cell nucleus extract, a double-stranded DNA having a transcription factor NF-κB-binding site is used as a fluorescently labeled double-stranded DNA, an amount of a cell nucleus extract solution is increased stepwise.

Another feature of the present invention is to extract a cell nucleus after adding a tumor necrosis factor TNF-α to the cell, and then mix the obtained cell nucleus extract and a fluorescently labeled double-stranded DNA, and to obtain a translational diffusion time of a substance having a fluorescent label in a mixed solution by fluorescence correlation spectroscopy. In the case where a transcriptional factor AP-1 is detected in a nucleus extract of HeLa cell, stimulation may be performed for 30 minutes with 50 ng/ml of a tumor necrosis factor TNF-α. In the case where a transcription factor AP-1 is detected in a nucleus extract of HeLa cell, stimulation may be performed for 15 minutes. The stimulation with a tumor necrosis factor TNF-α activates a transcription factor in a cell nucleus extract, and makes it easy to bind the activated transcription factor and the double-stranded DNA, and as a result, a transcription factor can be detected precisely.

Another feature of the present invention is to extract a cell nucleus after adding APDC and then a tumor necrosis factor TNF-α to the cell, and mix the obtained cell nucleus extract and a fluorescently labeled double-stranded DNA having a transcription factor AP-1-binding sequence, and to obtain a translational diffusion time of a substance having a fluorescent label in a mixed solution by fluorescence correlation spectroscopy. According to the present invention, the stimulation with APDC and a tumor necrosis factor TNF-α activates a transcription factor AP-1 in a cell nucleus extract, and makes it easy to bind the activated transcription factor and the double-stranded DNA, and as a result, a transcription factor AP-1 can be detected precisely. A time for stimulation with APDC may be 2 hours, and a time for stimulation with a tumor necrosis factor TNF-α may be 30 minutes.

Another feature of the present invention is to compare a translational diffusion time of a reaction product in the case of stimulation with only a tumor necrosis factor TNF-α, with a translational diffusion time of a reaction product in the case of stimulation with both APDC (Ammonium pyrrolidinedithiocarbamate) and a tumor necrosis factor TNF-α, when a transcription factor NF-κB is detected in a cell nucleus extract, based on a translational diffusion time of a reaction product resulting from the reaction of a transcription factor NF-κB and a fluorescently labeled double-stranded DNA having a transcription factor NF-κB-binding sequence. A tumor necrosis factor TNF-α activates a transcription factor NF-κB, and APDC suppresses activation of a transcription factor NF-κB. Therefore, if a translational diffusion time is greater in the case of the stimulation with only a tumor necrosis factor TNF-α, it can be the that a transcription factor NF-κB is contained in a cell nucleus extract. According to this feature, a transcription factor NF-κB can be detected precisely.

When the particle number in a confocal volume is 2 to 5 at the time of FCS measurement, FCS measurement can be performed precisely, and thus a binding reaction between a double-stranded DNA and a DNA-binding protein can be detected precisely. In particular, even when the particle number in a confocal volume is 2 to 3, precise detection is possible. Therefore, the detection method of the present invention is suitable also when a large amount of a double-stranded DNA or a DNA-binding protein can not be prepared, or when detection result is desired with only a small amount of a sample.

In addition, according to the present invention, even when a crude sample such as an unpurified cell nucleus extract is used, a binding reaction between a double-stranded DNA and a transcription factor can be detected precisely. Further, according to the present invention, a reaction product resulting from an inherent double-stranded DNA and a transcription factor can be detected without preventing a binding reaction between them, even in the presence of a double-stranded DNA which is different, only by one base or two bases, from the inherent double-stranded DNA to which a transcription factor inherently binds. Therefore, a measuring method by FCS according to the present invention is useful for detecting a particular DNA-binding protein (such as transcription factor or intranuclear receptor) present in a crude sample such as a cell nucleus extract.

BRIEF DESCRIPTION OF THE SEVERAL VIEWS OF THE DRAWING

FIG. 1 shows outline of a procedure and a product of Experiment 1-1. (1) FCS measurement of an unreacted double-stranded DNA (reference numeral 10) is performed. (2) A transcription factor TFIID (reference numeral 1) is added. (3) A transcription factor TFIIB (reference numeral 2) is added. (4) An anti-TFIIB antibody (reference numeral 3) is added.

FIG. 7 shows a vicinity of an objective lens 11 in Example 2.

FIG. 11 is a graph showing a translational diffusion time of a product (DNA-AP-1 complex) relative to a concentration of an (unlabeled) double-stranded DNA in Experiment 2-2, and a translational diffusion time of a product (DNA-AP-1 complex) relative to a concentration of an (unlabeled) DNA having no AP-1-binding sequence in Experiment 2-3.

FIG. 17 is a graph showing a translational diffusion time of a product (DNA-protein complex) relative to a concentration of (unlabeled) each double-stranded DNA in Experiments 5-1 to 5-3.

FIG. 20 is a graph showing a translational diffusion time of a product (DNA-AP-1 complex) relative to a concentration of added TNF-α and a concentration of added APDC in Experiment 7-1. (i) Stimulation with only a tumor necrosis factor TNF-α (concentration is 0 ng/mL). (ii) Stimulation with only a tumor necrosis factor TNF-α (concentration is 10 ng/mL). (iii) Stimulation with only a tumor necrosis factor TNF-α (concentration is 25 ng/mL). (iv) Stimulation with only a tumor necrosis factor TNF-α (concentration is 50 ng/mL). (v) Stimulation with APDC (concentration is 10 μM) and a tumor necrosis factor TNF-α (concentration is 50 ng/mL). (vi) Stimulation with APDC (concentration is 100 μM) and a tumor necrosis factor TNF-α (concentration is 50 ng/mL). (vii) Stimulation with APDC (concentration is 200 μM) and a tumor necrosis factor TNF-α (concentration is 50 ng/mL).

FIG. 21 is a graph showing a translational diffusion time of a product (DNA-NF-κB complex) relative to a concentration of added TNF-α and a concentration of added APDC in Experiment 7-2. (i) Stimulation with only a tumor necrosis factor TNF-α (concentration is 0 ng/mL). (ii) Stimulation with only a tumor necrosis factor TNF-α (concentration is 10 ng/mL). (iii) Stimulation with only a tumor necrosis factor TNF-α (concentration is 25 ng/mL). (iv) Stimulation with only a tumor necrosis factor TNF-α (concentration is 50 ng/mL). (v) Stimulation with APDC (concentration is 10 μM) and a tumor necrosis factor TNF-α (concentration is 50 ng/mL). (vi) Stimulation with APDC (concentration is 100 μM) and a tumor necrosis factor TNF-α (concentration is 50 ng/mL). (vii) Stimulation with APDC (concentration is 200 μM) and a tumor necrosis factor TNF-α (concentration is 50 ng/mL).

Figure 2:
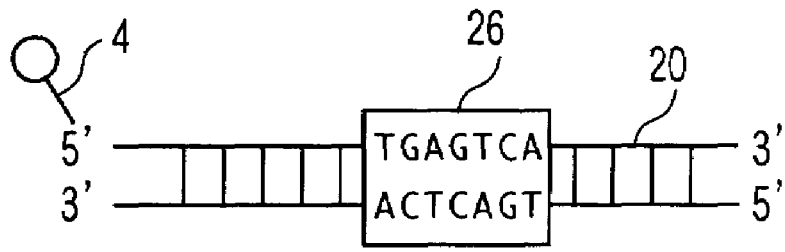
FIG. 2 shows outline of a procedure and a product of Experiment 2-1. (1) FCS measurement of an unreacted double-stranded DNA (reference numeral 20) is performed. (2) A transcription factor AP-1 (reference numeral 5) is added.
Figure 2:
Figure 2:
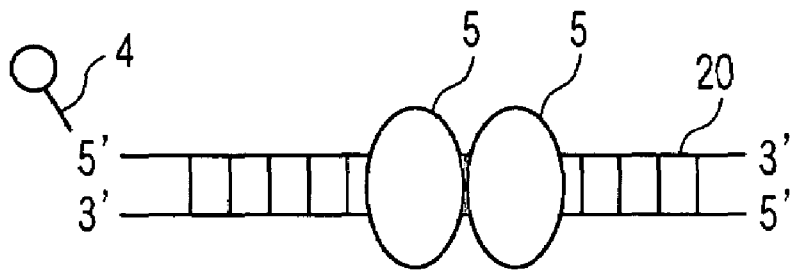
Figure 2:

Reference numerals in the figures denotes as follows:
1 . . . transcription factor TFIID;
2 . . . transcription factor TFIIB;
3 . . . anti-TFIIB antibody;
4 . . . fluorescent label;
5 . . . transcription factor AP-1;
10 . . . double-stranded DNA;
11 . . . oligo DNA;
12 . . . oligo DNA;
16 . . . binding site;
17 . . . double-stranded DNA;
18 . . . double-stranded DNA;
20 . . . double-stranded DNA;
21 . . . oligo DNA;
22 . . . oligo DNA;
24 . . . double-stranded DNA;
25 . . . double-stranded DNA;
26 . . . binding site;
26' . . . binding site different by two bases;
30 . . . double-stranded DNA;
31 . . . oligo DNA;
32 . . . oligo DNA;
33 . . . binding site;
33' . . . binding site different by one base;
34 . . . double-stranded DNA;
35 . . . double-stranded DNA.

DETAILED DESCRIPTION OF THE INVENTION

In embodiments of the present invention, various experiments are performed for detecting binding of a DNA and a protein which binds to a particular sequence part in a DNA (hereinafter, referred to as DNA binding protein). Embodiments will be explained as an example by each purpose of experiments. In experiments, after a process of a reaction of a biomolecule, FCS measurement is performed, and a translational diffusion time of the biomolecule is obtained.

Since a magnitude of a translational diffusion time shows a magnitude of a molecular weight, increase or decrease in a molecular weight is seen by comparing a translational diffusion time before and after a reaction. Increase in a molecular weight shows a binding reaction between biomolecules, decrease in a molecular weight shows a degradation reaction of a biomolecule, and maintenance of a molecular weight shows that there was neither binding nor degradation in a biomolecule.

Therefore, a binding reaction between a DNA and a DNA-binding protein can be detected by detecting increase in a translational diffusion time of a DNA after a reaction of a DNA and a DNA-binding protein, compared with a translational diffusion time of the DNA before the reaction.

According to the present invention, information for obtaining a translational diffusion time is obtained by mixing solutions and measuring by fluorescence correlation spectroscopy. As a result, a reaction of a DNA and a DNA-binding protein can be detected simply and in a short time, without performing troublesome operation such as utilization of a radioisotope and selection by an electrophoresis method, and immobilization of a molecule on a solid substrate.

In addition, according to the present invention, even when a crude sample such as a cell nucleus extract which has not been purified is used, a binding reaction of a double-stranded DNA and a transcription factor can be detected precisely. Further, according to the present invention, a reaction product resulting from an inherent double-stranded DNA and a transcription factor can be detected without preventing a binding reaction between them, even in the presence of a double-stranded DNA which is different, only by one base or two bases, from the inherent double-stranded DNA to which a transcription factor inherently binds. Therefore, a measuring method by FCS according to the present invention is useful for detecting a particular DNA-binding protein (such as transcription factor or intranuclear receptor) present in a crude sample such as a cell nucleus extract.

EXAMPLES

Summary of experimental contents and experimental results of each Example is shown in Tables 1 to 4, and detail of each Example will be explained later.

TABLE 1

Summary of experimental contents and experimental results of Examples

Figure 8:
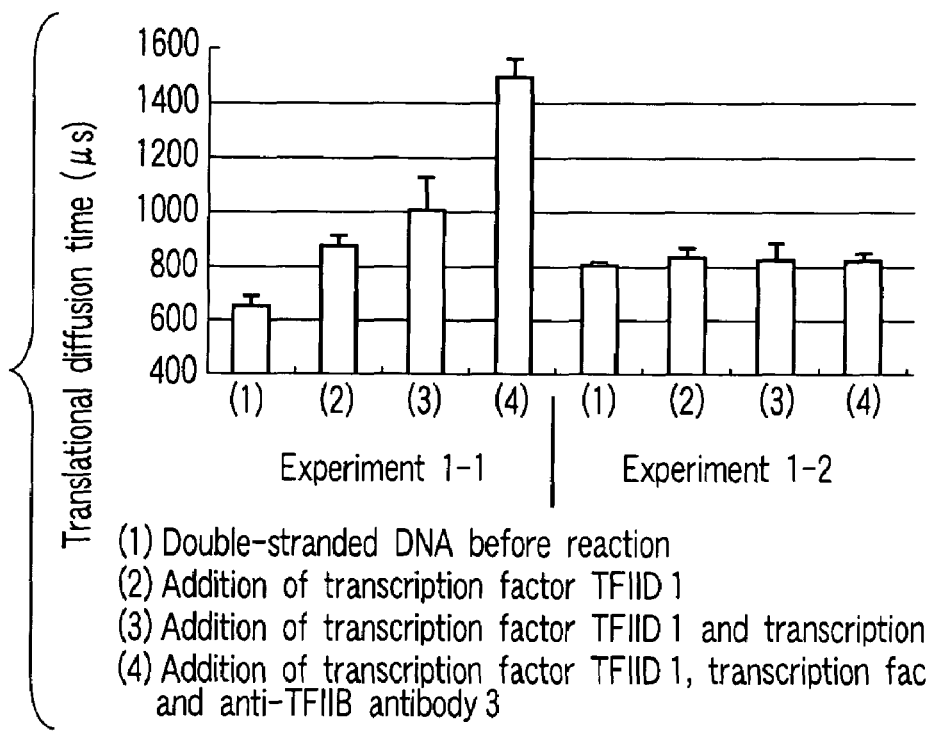
FIG. 8 is a graph showing a translational diffusion time of a product (DNA-protein complex) after each reaction in Experiments 1-1 and 1-2. Reference numeral (1) denotes a translational diffusion time of a double-stranded DNA before a reaction; reference numeral (2) denotes the case where a transcription factor TFIID is added; reference numeral (3) denotes the case where a transcription factor TFIID and a transcription factor TFIIB are added; and reference numeral (4) denotes the case where a transcription factor TFIID, a transcription factor TFIIB and an anti-TFIIB antibody are added.
Figure 9:
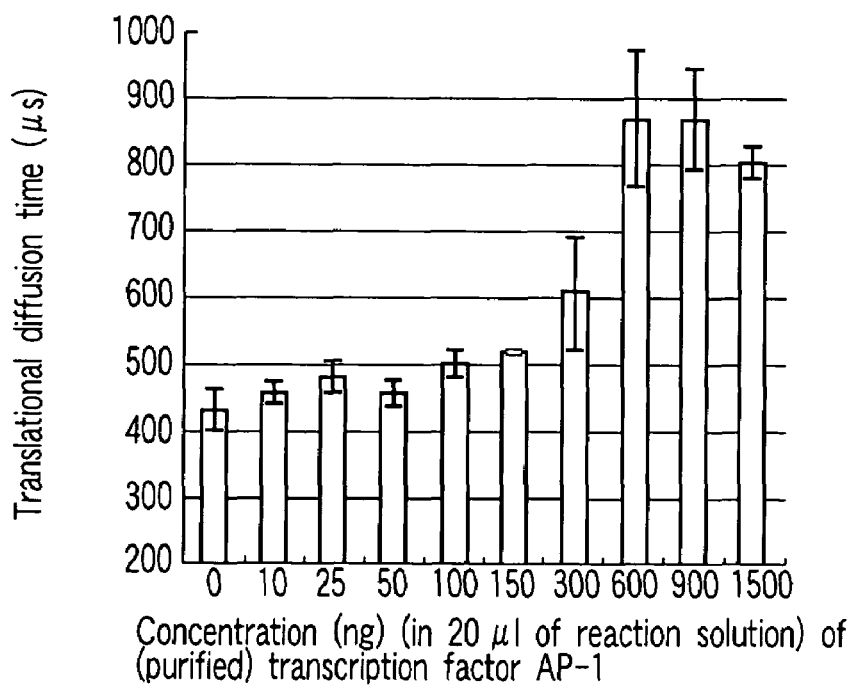
FIG. 9 is a graph of a translational diffusion time of a product (DNA-AP-1 complex) relative to a concentration of a transcription factor AP-1 in Experiment 2-1.
Figure 10:
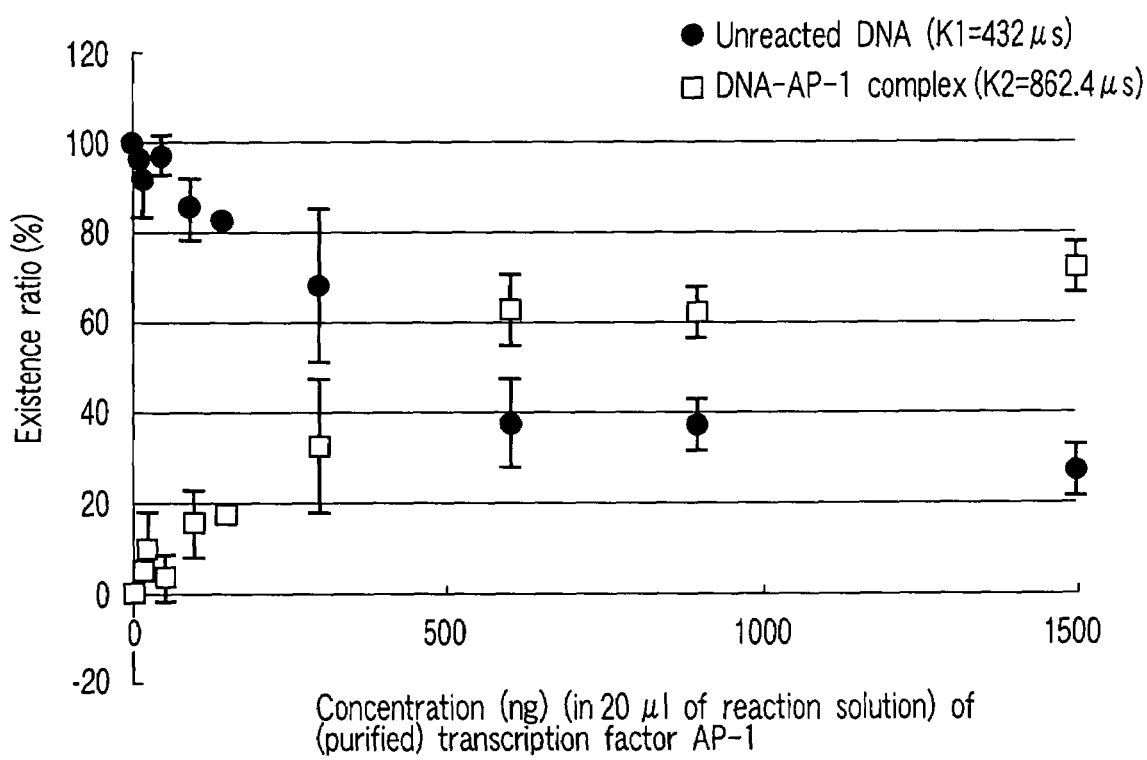
FIG. 10 is a graph showing an existence ratio of an unreacted product (unreacted DNA: K1) and a reaction product (DNA-AP-1 complex: K2) relative to a concentration of a transcription factor AP-1 in Experiment 2-1.

| | Experiment | Content | Result |
|---|---|---|---|
| | | Experiment for detecting a binding reaction of a DNA and a DNA-binding protein | |
| Example 1 | 1-1 | Experiment of a reaction of a (fluorescently labeled) DNA having a TFIID-binding sequence, a transcription factor TFIID, a transcription factor TFIIB and an anti-TFIIB antibody | FIG. 8: a graph showing a translational diffusion time of a DNA-protein complex after each reaction |
| | 1-2 | Experiment of a reaction of a (fluorescently labeled) DNA having no TFIID-binding sequence, a transcription factor TFIID, a transcription factor TFIIB and an anti-TFIIB antibody | |
| | | Experiment for detecting dependency on a concentration of a transcription factor AP-1, regarding a binding reaction of a DNA and a transcription factor AP-1 | |
| Example 2 | 2-1 | Experiment of a reaction of a (fluorescently labeled) DNA having an AP-1-binding sequence and a transcription factor AP-1. Experiment by stepwise changing a concentration of the transcription factor AP-1. | FIG. 9: a graph showing a translational diffusion time of a DNA-AP-1 complex relative to a concentration of a transcription factor AP-1 FIG. 10: a graph showing an existence ratio of an unreacted DNA and a DNA-AP-1 complex relative to a concentration of a transcription factor AP-1 |
| | 2-2 | Experiment of a reaction of a (fluorescently labeled) DNA having an AP-1-binding sequence and a transcription factor AP-1, when an (unlabeled) double-stranded DNA having an AP-1-binding sequence is added. Experiment by stepwise changing a concentration of the (unlabeled) double-stranded DNA. | FIG. 11: a graph showing a translational diffusion time of a DNA-AP-1 complex relative to a concentration of an (unlabeled) added DNA, and a translational diffusion time of a DNA-AP-1 complex relative to a concentration of an (unlabeled) DNA having no AP-1-binding sequence |
| | 2-3 | Experiment of a reaction of an (unlabeled) DNA having no AP-1-binding sequence and a transcription factor AP-1. Experiment by stepwise changing a concentration of the (unlabeled) DNA having no AP-1-binding sequence. | |

TABLE 2

Summary of experimental contents and experimental results of respective Examples (continued from Table 1)

Figure 12:
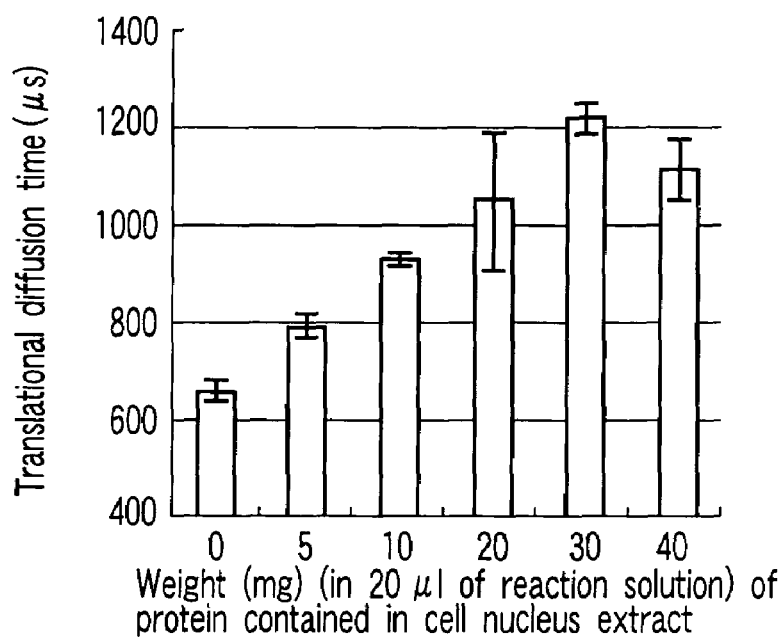
FIG. 12 is a graph showing a translational diffusion time of a product (DNA-AP-1 complex) relative to a concentration of a cell nucleus extract in Experiment 3-1.

| | Experiment | Content | Result |
|---|---|---|---|
| | | Experiment for detecting dependency on a concentration of a cell nucleus extract, regarding a binding reaction of a DNA and a cell nucleus extract | |
| Example 3 | 3-1 | Experiment of a reaction of a (fluorescently labeled) DNA having an AP-1-binding | FIG. 12: a graph showing a translational diffusion time of a DNA-AP-1 complex relative to a concentration of a cell |

TABLE 2-continued

Summary of experimental contents and experimental results of respective Examples (continued from Table 1)

Figure 13:
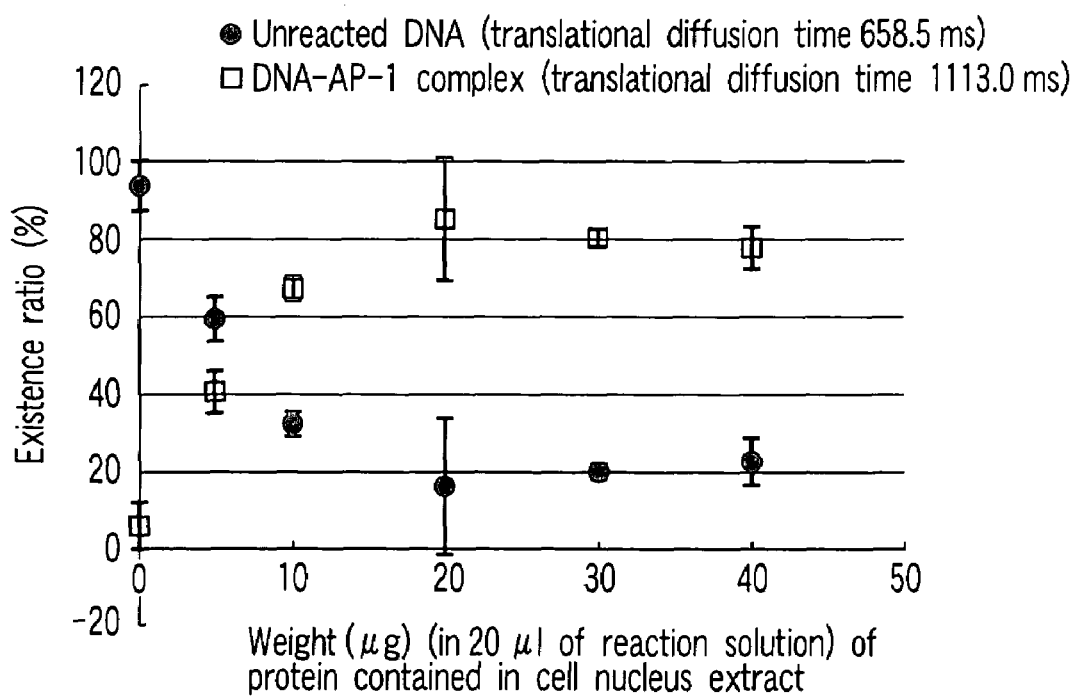
FIG. 13 is a graph showing an existence ratio of an unreacted product (unreacted DNA) and a product (DNA-AP-1 complex) relative to a concentration of a cell nucleus extract in Experiment 3-1.
Figure 14:
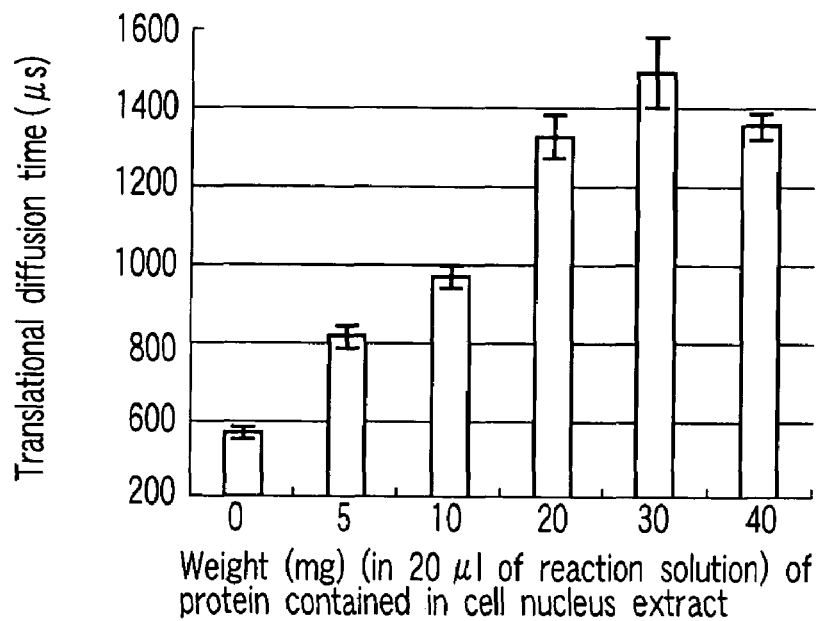
FIG. 14 is a graph showing a translational diffusion time of a product (DNA-NF-κB complex) relative to a concentration of a cell nucleus extract in Experiment 3-2.

| Experiment | | Content | Result |
|---|---|---|---|
| | | sequence and a cell nucleus extract. Experiment by stepwise changing a concentration of the cell nucleus extract. | nucleus extract<br>FIG. 13: a graph showing an existence ratio of an unreacted DNA and a DNA-AP-1 complex relative to a concentration of a cell nucleus extract |
| | 3-2 | Experiment of a reaction of a (fluorescently labeled) DNA having an NF-κB-binding sequence and a cell nucleus extract. Experiment by stepwise changing a concentration of the cell nucleus extract. | FIG. 14: a graph showing a translational diffusion time of a DNA-NF-κB complex relative to a concentration of a cell nucleus extract<br>FIG. 15: a graph showing an existence ratio of an unreacted DNA and a DNA-NF-κB complex relative to a concentration of a cell nucleus extract |

TABLE 3

Summary of experimental contents and experimental results of respective Examples (continued from Table 2)

| | Experiment | Content | Result |
|---|---|---|---|
| | | Experiment for detecting a binding reaction of a DNA having an AP-1-binding sequence and a cell nucleus extract, when a double-stranded DNA is added | |
| Example 4 | 4-1 | Experiment of a reaction of a (fluorescently labeled) DNA having an AP-1-binding sequence and a cell nucleus extract, when an (unlabeled) double-stranded DNA having an AP-1-binding sequence is added. Experiment by stepwise changing a concentration of the (unlabeled) double-stranded DNA. | FIG. 16: a graph showing a translational diffusion time of a DNA-protein complex relative to a concentration of (unlabeled) each double-stranded DNA |
| | 4-2 | Experiment of a reaction of a (fluorescently labeled) DNA having an AP-1-binding sequence and a cell nucleus extract, when an (unlabeled) double-stranded DNA having a sequence which is different from the AP-1-binding sequence by only two bases is added. Experiment by stepwise changing a concentration of the (unlabeled) double-stranded DNA. | |
| | 4-3 | Experiment of a reaction of a (fluorescently labeled) DNA having an AP-1-binding sequence and a cell nucleus extract, when an (unlabeled) double-stranded DNA having no AP-1-binding sequence is added. Experiment by stepwise changing a concentration of the (unlabeled) double-stranded DNA. | |
| | | Experiment for detecting a binding reaction of a DNA having an NF-κB-binding sequence and a cell nucleus extract, when a double-stranded DNA is added | |
| Example 5 | 5-1 | Experiment of a reaction of a (fluorescently labeled) DNA having an NF-κB-binding sequence and a cell nucleus extract, when an (unlabeled) double-stranded DNA having an NF-κB-binding sequence is added. Experiment by stepwise changing a concentration of the (unlabeled) double-stranded DNA. | FIG. 17: a graph showing a translational diffusion time of a DNA-protein complex relative to a concentration of (unlabled) each double-stranded DNA |
| | 5-2 | Experiment of a reaction of a (fluorescently labeled) DNA having an NF-κB-binding sequence and a cell nucleus extract, when an (unlabeled) double-stranded DNA having a sequence which is different from an NF-κB-binding sequence by only one base is added. Experiment by stepwise changing a concentration of the (unlabeled) double-stranded DNA. | |
| | 5-3 | Experiment of a reaction of a (labeled) DNA having an NF-κB-binding sequence and a cell nucleus extract, when an (unlabeled) double-stranded DNA having no NF-κB-binding sequence is added. Experiment by stepwise changing a concentration of the (unlabeled) double-stranded DNA. | |

TABLE 4

Summary of experimental contents and experimental results of respective Examples (continued from Table 3)

| | Experiment | Content | Result |
|---|---|---|---|
| | | Experiment for detecting dependency on stimulation with a tumor necrosis factor TNF-α at the time of extraction of a cell nucleus, regarding activation of a transcription factor in the cell nucleus | |
| Example 6 | 6-1 | Experiment of a reaction of a (fluorescently labeled) DNA having an AP-1-binding sequence and a cell nucleus extract. Experiment by use of a cell nucleus extract which is extracted under the condition of a different time length of stimulation with a tumor necrosis factor TNF-α. | FIG. 18: a graph showing a translational diffusion time of a DNA-AP-1 complex relative to a stimulation time |

TABLE 4-continued

Summary of experimental contents and experimental results of respective Examples
(continued from Table 3)

| Experiment | | Content | Result |
|---|---|---|---|
| | 6-2 | Experiment of a reaction of a (fluorescently labeled) DNA having an NF-κB-binding sequence and a cell nucleus extract. Experiment by use of a cell nucleus extract which is extracted under the condition of a different time length of stimulation with a tumor necrosis factor TNF-α. | FIG. 19: a graph showing a translational diffusion time of a DNA-NF-κB complex relative to a stimulation time |
| | | Experiment for detecting dependency on stimulation with a tumor necrosis factor TNF-α and an NF-κB activity inhibitor APDC at the time of extraction of a cell nucleus, regarding activation of a transcription factor in the cell nucleus | |
| Example 7 | 7-1 | Experiment of a reaction of a (fluorescently labeled) DNA having an AP-1-binding sequence and a cell nucleus extract. Experiment by use of a cell nucleus extract which is extracted under the condition of a different concentration of an added tumor necrosis factor TNF-α and a different concentration of an added NF-κB activity inhibitor APDC. | FIG. 20: a graph showing a translational diffusion time of a DNA-AP-1 complex relative to a concentration of added TNF-α and a concentration of added APDC |
| | 7-2 | Experiment of a reaction of a (fluorescently labeled) DNA having an NF-κB-binding sequence and a cell nucleus extract. Experiment by use of a cell nucleus extract which is extracted under the condition of a different concentration of added tumor necrosis factor TNF-α and a different concentration of added NFκB activity inhibitor APDC. | FIG. 21: a graph showing a translational diffusion time of a DNA-NF-κB complex relative to a concentration of added TNF-α and a concentration of added APDC. |

Example 1

In the present Example, a binding reaction of a DNA, and a transcription factor TFIID and a transcription factor TFIIB which are a DNA-binding protein is detected.

Figure 5:
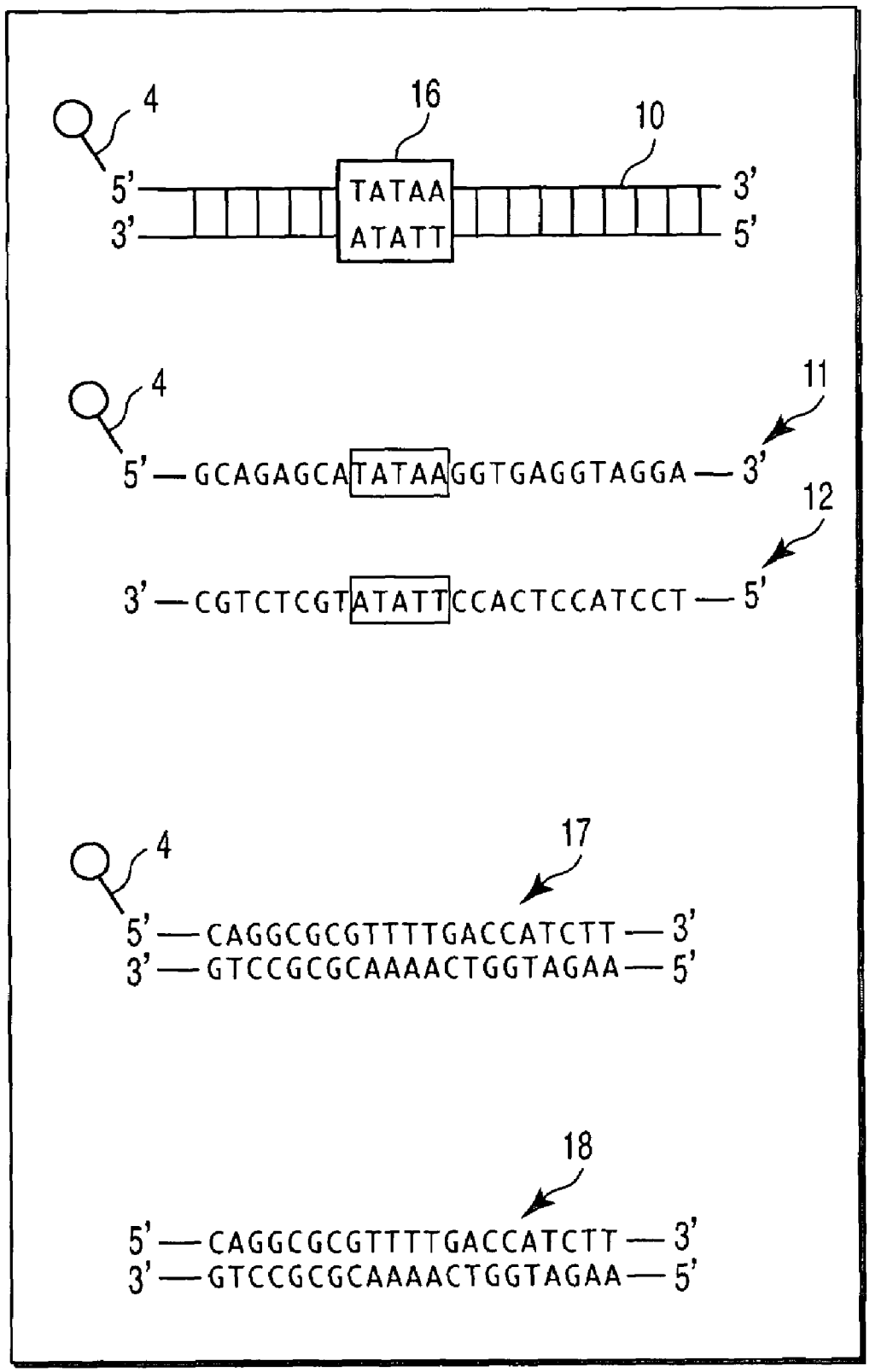
FIG. 5 shows a DNA used in each experiment.

As a DNA, a double-stranded DNA 10 shown in FIG. 5 is used. The double-stranded DNA 10 consists of an oligo DNA 11 which has been labeled with a fluorescent label 4 (TAMRA label) at a 5'-terminal, and an oligo DNA 12 having a nucleotide sequence complementary to that of the oligo DNA 11. The double-stranded DNA 10 has a TATAA sequence (a complementary sequence is an ATATT sequence), which is a binding site 16 to which a transcription factor TFIID and a transcription factor TFIIB bind.

As a DNA-binding protein, a transcription factor TFIID 1 containing TBP (TATA binding protein) and a transcription factor TFIIB 2 are used. Further, as an antibody which binds to a transcription factor TFIIB 2, an anti-TFIIB antibody 3 is used.

As a transcription factor TFIID 1, a transcription factor TFIIB 2 and an anti-TFIIB antibody 3, the following shown in Table 5 are used. A length of a double-stranded DNA 10 is suitably 100 bp or less, particularly desirably 10 to 50 bp. When a length of a double-stranded DNA is in this range, result of FCS measurement is obtained precisely, because an incremental ratio of a molecular weight of the double-stranded DNA is sufficiently great in the case where the double-stranded DNA binds to a transcription factor.

TABLE 5

| Transcription factor/antibody | Concentration | English name and others |
|---|---|---|
| Transcription factor TFIID 1 | 50 ng/μl | TFIID(TBP) (manufactured by Santa Cruze Biotechnology. Inc sc-4000) |

TABLE 5-continued

| Transcription factor/antibody | Concentration | English name and others |
|---|---|---|
| Transcription factor TFIIB 2 | 170 ng/μl | TFIIB human recombinant (manufactured by Promega E3790) |
| Anti-TFIIB antibody 3 | 200 μg/ml | Anti-Human TFIIB IgG mAb (manufactured by Promega E3838A) |

<Preparation and Adjustment of Double-stranded DNA 10>

First, a double-stranded DNA 10 used in detection experiment is prepared. For preparing the double-stranded DNA 10, the following shown in Table 6 are used.

TABLE 6

| | Concentration | Amount | English name and others |
|---|---|---|---|
| Oligo DNA 11 (labeled with a fluorescent label) | 100 nM | | |
| Oligo DNA 12 | 100 nM | | |
| STE buffer (NaCl/TE) | 100 mM | | |
| 3' → 5' Exonuclease I | | 1 μl relative to 100 μl of reaction solution | Exonuclease I (EPICENTRE X40501K), Polynucleotide terminal hydrolytic enzyme |
| MgCl$_2$ | 1M | 1 μl relative to 100 μl reaction solution | |
| dW | | Suitable amount | Deionized water |

The oligo DNA 11 and the oligo DNA 12 are reacted in the STE buffer, and the reaction is heated at 95° C. for 5 minutes, and slowly cooled to 20° C. Then, the reaction solution is allowed to stand in a PCR instrument or at room temperature to cause annealing of the oligo DNAs. Exonuclease I and MgCl$_2$ are added to the annealed reaction solution, followed by a reaction at 37° C. for 1 hour. Added amounts of Exonuclease I and MgCl$_2$ are 1 μl relative to 100 μl of the reaction solution, respectively. Thereafter, the reaction solution is purified with a purification kit MERmaid SPIN (BIO 101), and a double-stranded DNA 10 consisting of an oligo DNA 11 and an oligo DNA 12 is extracted with dW.

The extracted double-stranded DNA 10 is measured by fluorescence correlation spectroscopy (FCS), and diluted with dW so as to be around 20 of the particle number (n), thereby preparing a solution of a double-stranded DNA 10 (a concentration of the double-stranded DNA 10 in the solution is 2 nM to 5 nM). When each experiment is performed using the solution of a double-stranded DNA having the particle number (n) of around 20, the particle number in a confocal volume is 2 to 5 at the time of FCS measurement. As a result, FCS measurement is performed precisely, and a binding reaction of a double-stranded DNA and a DNA-binding protein can be detected precisely.

[Experiment 1-1] Experiment of a reaction of a (fluorescently labeled) DNA having a TFIID-binding sequence with a transcription factor TFIID, a transcription factor TFIIB and an anti-TFIIB antibody FIG. 1 shows outline of a procedure and a product of Experiment 1-1. FCS measurement was performed five times after every reaction under the condition of irradiation of laser light at a wavelength of 543 nm and an output of 100 μW for 15 seconds per one time.

(1) FCS Measurement of an Unreacted Double-stranded DNA 10

The following solution shown in Table 7 is placed in a container, stirred gently with a tip of a chip, slightly tapped, and allowed to stand at room temperature for 30 minutes. Then, FCS measurement is performed to obtain a translational diffusion time.

TABLE 7

|  | Concentration | Amount (total 20 μl) |
|---|---|---|
| Fluorescently labeled double-stranded DNA 10 |  | 5 μl |
| 5 × binding buffer |  | 4 μl |
| dW |  | 10 μl |
| Buffer for TFIID |  | 1 μl |

TABLE 8

Composition of 5 × binding buffer

|  | Concentration | English name and others |
|---|---|---|
| Tris-hydrochloride pH 7.5 | 250 mM | Tris-HCl |
| Potassium chloride | 350 mM | KCl |
| EDTA | 5 mM | Ethylenediaminetetraacetic acid |
| 2-Mercaptoethanol | 5 mM | 2-Mercaptoethanol |
| BSA | 1 mg/ml | Bovine serum albumin |
| Glycerol | 50% concentration | Glycerol |

TABLE 9

Composition of buffer for TFIID

|  | Concentration | English name and others |
|---|---|---|
| DTT | 5 mM | Dithiothreitol |
| Glycerol/PBS | 50% concentration | Glycerol/PBS (phosphate buffered saline) |

A DNA-binding protein is not added at this stage, and thus a DNA-protein complex is not formed, and a double-stranded DNA 10 remains unreacted.

(2) Reaction of a Double-stranded DNA 10 and a Transcription Factor TFIID 1

The following solution shown in Table 10 is placed in a container, stirred gently with a tip of a chip, slightly tapped, and allowed to stand at room temperature for 30 minutes. Then, FCS measurement is performed to obtain a translational diffusion time. A transcription factor TFIID has been adjusted with a buffer for TFIID to 25 ng/μl in advance.

TABLE 10

|  | Concentration | Amount (total 20 μl) |
|---|---|---|
| Fluorescently labeled double-stranded DNA 10 |  | 5 μl |
| Transcription factor TFIID 1 | 25 ng/μl | 1 μl |
| dW |  | 10 μl |
| 5 × binding buffer |  | 4 μl |

The obtained product is a DNA-protein complex in which a transcription factor TFIID 1 is bound to a binding site 16 of a double-stranded DNA 10.

(3) Reaction of the Reacted Solution of (2) and a Transcription Factor TFIIB 2

1 μl of 85 ng/μl transcription factor TFIIB 2 is added to 20 μl of the reacted solution (2), gently mixed with a tip of a chip, slightly tapped, and allowed to stand at room temperature for 20 minutes. Then, FCS measurement is performed to obtain a translational diffusion time.

The product is a DNA-protein complex in which a transcription factor TFIID 1 and a transcription factor TFIIB 2 are bound to a binding site 16 of a double-stranded DNA 10.

(4) Reaction of the Reacted Solution of (3) and an Anti-TFIIB Antibody 3

1 μl of an anti-TFIIB antibody 3 is added to 20 μl of the reacted solution of (3), gently mixed with a tip of a chip, slightly tapped, and allowed to stand at room temperature for 20 minutes. Then, FCS measurement is performed to obtain a translational diffusion time.

The product is a DNA-protein complex in which a transcription factor TFIID 1 and a transcription factor TFIIB 2 are bound to a binding site 16 of a double-stranded DNA 10, and an anti-TFIIB antibody 3 is further bound to a transcription factor to TFIIB 2.

[Experiment 1-2] Experiment of a reaction of a (fluorescently labeled) DNA having no TFIID-binding sequence with a transcription factor TFIID, a transcription factor TFIIB and an anti-TFIIB antibody The same reaction experiment as Experiment 1-1 (1) to (4) was performed using an *Escherichia coli*-derived double-stranded random sequence DNA 17, which dose not contain a binding site 16 to which a transcription factor TFIID binds, in place of a double-stranded DNA 10.

Translational diffusion times of the products obtained in Experiments 1-1 and 1-2 are shown in FIG. 8. In Experiment 1-1 using a double stranded DNA 10, a translational diffusion time of a DNA-protein complex after each reaction is greater as compared with a translational diffusion time of a double-stranded DNA 10 before the reaction. The result shows that the double-stranded DNA 10 is bound to a translational factor TFIID 1, a transcription factor TFIIB 2 and an anti-TFIIB antibody 3. On the other hand, in Experiment 1-2 using an *Escherichia coli*-derived double-stranded random sequence DNA 17, a change in a translational diffusion time is little in any case, and binding of the DNA with a DNA-binding protein could not be confirmed. In particular, a translational diffusion time of a DNA-protein complex in which all of three proteins of a transcriptional factor TFIID 1, a transcription factor TFIIB 2 and an anti-TFIIB antibody 3 are bound is remarkably greater than a translational diffusion time of other DNA-protein complex.

Therefore, in the case of detecting whether or not a binding site 16 for a transcription factor TFIID 1 and a transcription factor TFIIB 2 is present in a fluorescently labeled DNA, the presence of a binding site 16 can be detected precisely by adding all of a transcription factor TFIID 1, a transcription factor TFIIB 2 and an anti-TFIIB antibody 3 to a DNA containing solution, and measuring a DNA-protein complex by FCS to obtain a translational diffusion time.

In addition, in the case of detecting whether or not a transcription factor TFIID 1 is present in a solution containing some kind of DNA-binding protein, the presence of a transcription factor TFIID 1 can be detected precisely by adding a transcription factor TFIIB 2 and an anti-TFIIB antibody 3 together with a fluorescently labeled double-stranded DNA 10 having a binding site 16 to a reaction solution, and measuring a DNA-protein complex by FCS to obtain a translational diffusion time.

Example 2

In the present Example, regarding a binding reaction of a DNA and a transcription factor AP-1 which is a DNA-binding protein, dependency on a concentration of a transcription factor AP-1 is examined.

Figure 6:
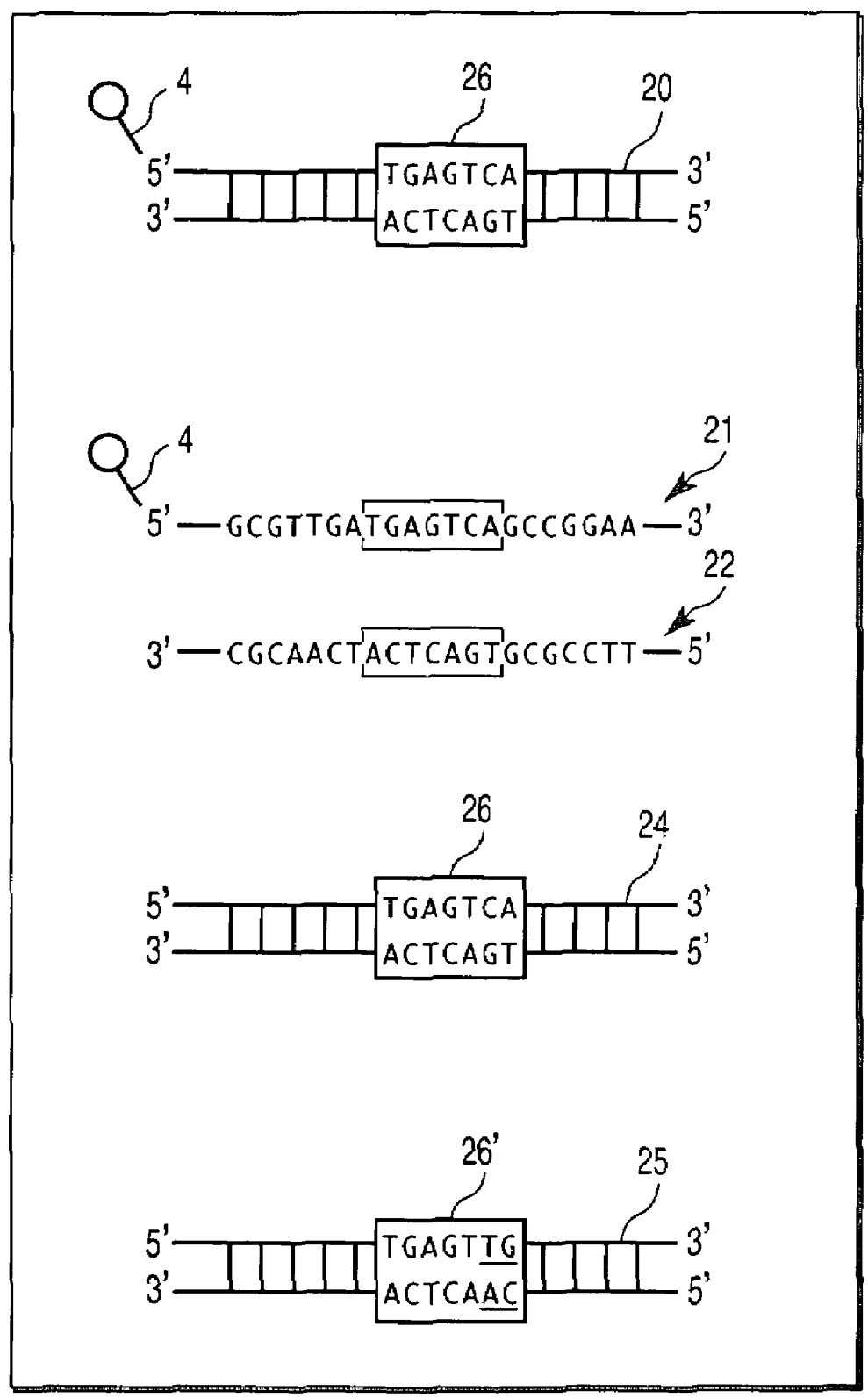
FIG. 6 shows a DNA used in each experiment.

As a DNA, a double-stranded DNA 20 shown in FIG. 6 is used. The double-stranded DNA 20 consists of an oligo DNA 21 having a fluorescent label 4 (TAMRA label) at a 5'-terminal, and an oligo DNA 22 having a nucleotide sequence complementary to that of the oligo DNA 21. The double-stranded DNA 20 has a TGAGTCA sequence (a complementary sequence is an ACTCAGT sequence), which is a binding site 26 to which a transcription factor AP-1 binds. A length of the double-stranded DNA 20 is suitably 100 bp or less, particularly desirably 10 to 50 bp. When a length of a double-stranded DNA is in this range, result of FCS measurement is obtained precisely, because an increment ratio of a molecular weight of a double-stranded DNA is great in the case where a double-stranded DNA is bound to a transcription factor or the like.

As a DNA-binding protein, the following transcription factor AP-1 5 shown in Table 11 is used.

TABLE 11

| Transcription factor/antibody | Molecular weight | English name and others |
|---|---|---|
| Transcription factor AP-1 5 | 40 kDa 80 kDa due to formation of dimer when bound to DNA | AP-1 (c-Jun, human) (manufactured by Promega E3061) |

<Preparation and Adjustment of Double-stranded DNA 20>

First, a double-stranded DNA 20 used in detection experiment is prepared. For preparing the double-stranded DNA 20, the following shown in Table 12 are used.

TABLE 12

| | Concentration | Amount | English name and others |
|---|---|---|---|
| Oligo DNA 21 (labeled with Fluorescent label) | | 100 nM | |
| Oligo DNA 22 | | 100 nM | |
| STE buffer (NaCl/TE) | | 100 mM | |
| 3' → 5' Exonuclease I | | 1 µl relative to 100 µl of reaction solution | Exonuclease I(EPICENTRE X40501K) Polynucleotide terminal hydrolytic enzyme |
| MgCl₂ | 1M | 1 µl relative to 100 µl of reaction solution | |
| dW | | Suitable amount | Deionized water |

The oligo DNA 21 and the oligo DNA 22 are reacted in the STE buffer, and the reaction is heated at 95° C. for 5 minutes, and slowly cooled to 20° C. Then, the reaction solution is allowed to stand in a PCR instrument or at room temperature to cause annealing of the oligo DNAS. Exonuclease I and MgCl₂ are added to the annealed reaction solution, followed by a reaction at 37° C. for 1 hour. Added amounts of Exonuclease I and MgCl₂ are 1 µl relative to 100 µl of the reaction solution, respectively. Thereafter, the reaction solution is purified by MERmaid SPIN (BIO 101), and a double-stranded DNA 20 consisting of an oligo DNA 21 and an oligo DNA 22 is extracted with dW.

The extracted double-stranded DNA 20 is measured by fluorescence correlation spectroscopy (FCS), and diluted with dW so as to be around 20 to 30 of the particle number (n), thereby preparing a solution of a double-stranded DNA 20.

An unlabeled double-stranded DNA 24 is prepared and extracted in the same way as the double-stranded DNA 20, by using an oligo DNA which has the same sequence but is not fluorescently labeled, in place of the oligo DNA 21 (labeled with a fluorescent label 4). An absorbance (OD260 value) of the extracted double-stranded DNA 24 is measured, and the extract is diluted with dW to an OD260 value of 20, thereby preparing a solution of a double-stranded DNA 24.

[Experiment 2-1] Experiment of a reaction of (fluorescently labeled) DNA having a AP-1-binding sequence and a transcription factor AP-1. The Experiment was performed by adding a transcription factor AP-1 at a different concentration.

FIG. 2 shows outline of a procedure and a product of Experiment 2-1. The following solution shown in Table 13 is placed in a container, gently stirred with a tip of a chip, slightly tapped, and reacted at 34° C. for 1 hour. Then, FCS measurement is performed to obtain a translational diffusion time. FCS measurement was performed five times after each reaction under the condition of irradiation of laser light at a wavelength of 543 nm and an output of 100 μW for 15 seconds per one time.

TABLE 13

|  | Concentration | Amount (total 20 μl) |
|---|---|---|
| Fluorescently labeled double-stranded DNA 20 |  | 2 μl |
| Transcription factor AP-1 5 | 0, 10, 25, 50, 100, 150, 300, 600, 900 or 1500 ng relative to total amount of 20 μl | 5 μl |
| dW |  | 9 μl |
| 5 × binding buffer (for transcription factor AP-1) |  | 4 μl |

TABLE 14

| Composition of 5 × binding buffer (for transcription factor AP-1) | | |
|---|---|---|
|  | Concentration | English name and others |
| Tris-HCl pH 7.5 | 250 mM | Tris-HCl |
| Potassium chloride | 350 mM | KCl |
| EDTA | 5 mM | Ethylenediaminetetraacetic acid |
| 2-Mercaptoethanol | 5 mM | 2-Mercaptoethanol |
| BSA | 1 mg/ml | Bovine serum albumin |
| Glycerol | 40% concentration | Glycerol |

In a reaction using a transcription factor AP-1 5 having a concentration of 0 ng/μl, a DNA-binding protein is not added, and thus a DNA-protein complex is not present, and a double-stranded DNA 20 remains unreacted (see FIG. 2 (1)). The product obtained after the reaction is a complex in which a transcription factor AP-1 5 is bound to a binding site 26 of a double-stranded DNA 20 (see FIG. 2 (2)). Regarding an unreacted double-stranded DNA 20 and products obtained at various concentration of transcription factor AP-1 5, results of FCS measurement are shown in Table 15.

At a concentration of a transcription factor AP-1 of 600 ng/μl, a translational diffusion time of the product was greatly extended, and concentration dependency was recognized. A difference in a translational diffusion time at a concentration of a transcription factor AP-1 from 600 ng/μl to 1500 ng/μl is small, as compared with a difference in a translational diffusion time at a concentration of up to 300 ng/μl. Accordingly it can be said that binding of a double-stranded DNA 20 and a transcription factor AP-1 5 approaches saturation at a concentration of 600 ng/μl (see FIG. 9).

In addition, an existence ratio of an unreacted double-stranded DNA 20 (K1) having a translational diffusion time of 432 μs and the product (K2) having a translational diffusion time of 862.4 μs is approximately constant at a concentration of a transcription factor AP-1 of 600 ng/μl or higher. Therefore, a binding reaction is sufficiently generated at a concentration of 600 ng/μl. When a concentration of a transcription factor AP-1 is 1500 ng/μl, it is thought that binding of a transcription factor AP-1 with a double-stranded DNA 20 having a constant concentration is in the saturated state (see FIG. 10).

[Experiment 2-2] Experiment of a reaction of a (fluorescently labeled) DNA having an AP-1-binding sequence and a transcription factor AP-1, when an (unlabeled) double-stranded DNA having an AP-1-binding sequence is added. The Experiment was performed by stepwise changing a concentration of the (unlabeled) double-stranded DNA.

Figure 3:
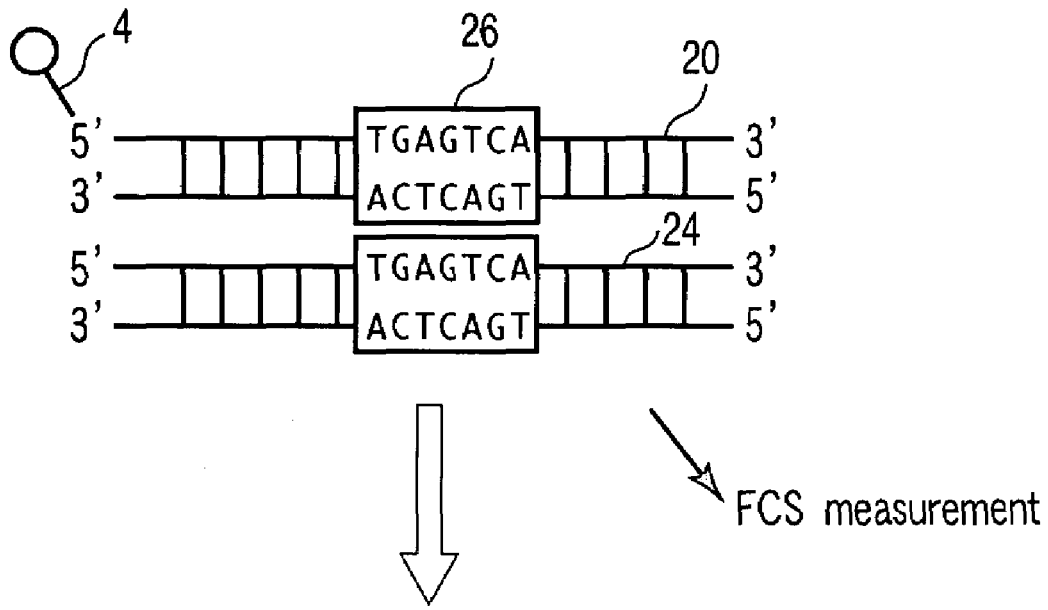
FIG. 3 shows outline of a procedure and a product of Experiment 2-2. (1) FCS measurement of an unreacted double-stranded DNA (reference numeral 20) is performed. (2) A transcription factor AP-1 (reference numeral 5) is added.
Figure 3:
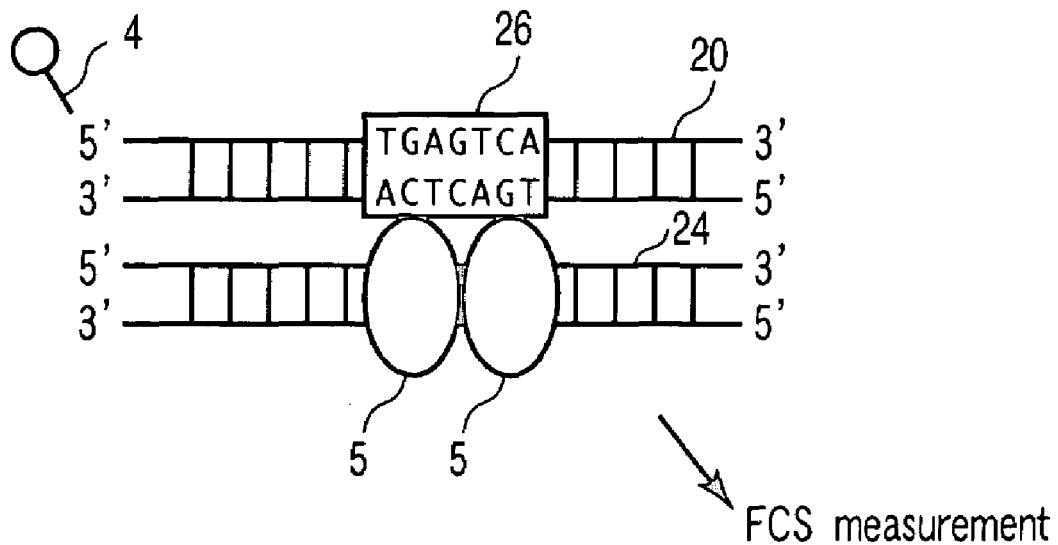

FIG. 3 shows outline of a procedure and a product of Experiment 2-2. As the (unlabeled) double-stranded DNA to be added, a double-stranded DNA 24 which has the same sequence as that of the double-stranded DNA 20 but is not labeled is used. A concentration of a transcription factor AP-1 5 is 600 ng/μl at which a binding reaction was sufficiently generated in Experiment 2-1.

The following solution shown in Table 16 is placed in a container, gently stirred with a tip of a chip, slightly tapped, and reacted at 34° C. for 1 hour. Then, FCS measurement is performed to obtain a translational diffusion time. FCS measurement was performed five times after each reaction under the condition of irradiation of laser light at a wavelength of 543 nm and an output of 100 μW for 15 seconds per one time.

TABLE 15

| Results of FCS measurement of DNA-AP-1 complex in Experiment 2-1 | | | | | | | | |
|---|---|---|---|---|---|---|---|---|
| Concentration of transcription factor AP-1 [μg] | Difft. K1 [μs] | SD Difft. K1 | CPP [kHz] | Frac. Triplet [%] | Triplet [μs] | CR [kHz] | SD Countrate [kHz] | n |
| 0 | 432 | 28.72 | 13.2 | 20.1 | 4.4 | 46.1 | 0.36 | 3.5 |
| 10 | 454.9 | 17.52 | 12.6 | 16.9 | 5.8 | 47.7 | 0.45 | 3.8 |
| 25 | 478.7 | 26.87 | 12.5 | 20.5 | 4.6 | 47 | 0.35 | 3.8 |
| 50 | 455.2 | 19.34 | 12.5 | 21.5 | 4.6 | 45 | 0.28 | 3.6 |
| 100 | 498.3 | 21.84 | 12.3 | 19 | 5.9 | 43.7 | 0.31 | 3.5 |
| 150 | 516.5 | 4.09 | 14.1 | 17 | 7.9 | 42.5 | 0.66 | 3 |
| 300 | 610.5 | 77.41 | 13.2 | 18 | 17.4 | 32.3 | 0.39 | 2.5 |
| 600 | 862.4 | 108.05 | 108.05 | 108.05 | 108.05 | 108.05 | 0.71 | 2.6 |
| 900 | 862.3 | 81.67 | 12.5 | 18.4 | 37.8 | 33.6 | 0.3 | 2.7 |
| 1500 | 798.9 | 27.05 | 10.8 | 18.8 | 6.4 | 38.2 | 0.74 | 3.5 |

TABLE 16

|  | Concentration | Amount (total 20 μl) |
|---|---|---|
| Fluorescently labeled double-stranded DNA 20 |  | 2 μl |
| Transcription factor AP-1 5 | 600 ng relative to total amount of 20 μl | 5 μl |
| Unlabeled double-stranded DNA 24 diluted with dW | 0, 10, 25, 50, 100, 150, 300, 600, 900 or 1500 ng relative to total amount of 20 μl | 10 μl |
| 5 × binding buffer (for transcription factor AP-1) |  | 4 μl |

[Experiment 2-3] Experiment of a reaction of an (unlabeled) DNA having no AP-1-binding sequence and a transcription factor AP-1. The Experiment was performed by stepwise changing a concentration of the (unlabeled) DNA having no AP-1-binding sequence.

Figure 4:
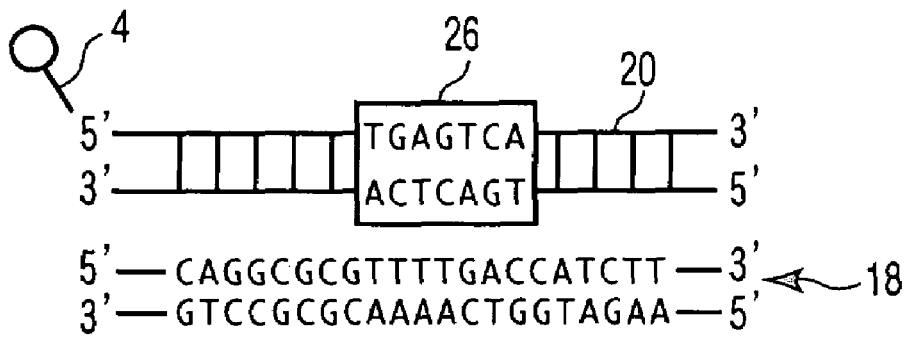
FIG. 4 shows outline of a procedure and a product of Experiment 2-3. (1) FCS measurement of an unreacted double-stranded DNA (reference numeral 20) is performed. (2) A transcription factor AP-1 (reference numeral 5) is added.
Figure 4:
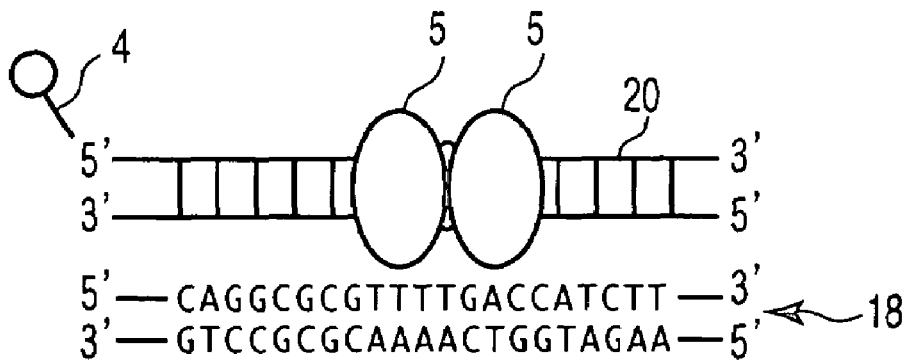

FIG. 4 shows outline of a procedure and a product of Experiment 2-3. As the (unlabeled) DNA to be added, a double-stranded DNA 18 which has an *Escherichia coli*-derived double-stranded random sequence having no AP-1-binding sequence and which has not been fluorescently labeled is used. A concentration of a transcription factor AP-1 5 is 600 ng/μl, at which a binding reaction is sufficiently generated in Experiment 2-1.

The following solution shown in Table 17 is placed in a container, gently stirred with a tip of a chip, slightly tapped, and reacted at 34° C. for 1 hour. Then, FCS measurement is performed to obtain a translational diffusion time. FCS measurement was performed five times after each reaction under the condition of irradiation of laser light at a wavelength of 543 nm and an output of 100 μW for 15 seconds per one time.

TABLE 17

|  | Concentration | Amount (total 20 μl) |
|---|---|---|
| Fluorescently labeled double-stranded DNA 20 |  | 2 μl |
| Transcription factor AP-1 5 | 600 ng relative to total amount of 20 μl | Amount corresponding to 5 μl |
| Unlabeled double-stranded DNA 18 diluted with dW | 25, 50, 100, 200, 300 or 600 ng relative to total amount of 20 μl | 10 μl |
| 5 × binding buffer (for transcription factor AP-1) |  | 4 μl |

From results of Experiment 2-2, a translational diffusion time of a DNA-protein complex of a double-stranded DNA 20 and a transcription factor AP-1 5 approached a transcription diffusion time of an unreacted DNA, by adding an unlabeled double-stranded DNA 24. Therefore, it was confirmed that binding of a double-stranded DNA 20 and a transcription factor AP-1 is inhibited (see FIG. 3 (2) and FIG. 11).

In addition, from results of Experiment 2-3, a transcriptional diffusion time of a DNA-protein complex of a double-stranded DNA 20 and a transcription factor AP-1 5 did not approach a translational diffusion time of an unreacted DNA, even when an unlabeled double-stranded DNA 18 was added (see FIG. 4 (2) and FIG. 11).

From results of competition assay performed in the above Experiment 2-2 and Experiment 2-3, it was demonstrated that a transcription factor AP-1 binds to a specific sequence of a double-stranded DNA.

In the case of detecting whether or not a transcription factor AP-1 is contained in a protein containing solution, the presence of a transcription factor AP-1 can be detected by stepwise adding a protein containing solution to a solution containing a fluorescently labeled double-stranded DNA, and measuring the product by FCS to obtain a translational diffusion time.

Example 3

In the present Example, regarding a binding reaction of a DNA and a transcription factor in a cell nucleus extract, dependency on a concentration of a cell nucleus extract is examined. As a DNA, the double-stranded DNA 20 used in Example 2 is used.

<Preparation of a Nucleus Extract from a Cell>

For preparing a nucleus extract from a cell, the following shown in Table 18 are used.

TABLE 18

| HeLa cell | English name and others |
|---|---|
| Medium D-MEM | Dulbecco's Modified Eagle's Medium (manufactured by Sigma D5796) |
| Phosphate buffered saline PBS (−) | phosphate buffered saline (GIBCO 21600-010) |
| Fetal bovine serum | Fetal Bovine Serum(GIBCO) |
| Recombinant human tumor necrosis factor TNF-α | Recombinant Human TNF-α (STARTHMANN BIOTEC AG) |
| DC protein Assay Kit | DC Protein Assay Kit (BIORAD 500-0116) |
| Protease inhibitor cocktail | Protease Inhibitor Cocktail (manufactured by Sigma P-1860) |

HeLa cells are put into the confluent state in a 10 cm dish. After the cells are washed with PBS(−) two times, a medium is exchanged with 0.5% FCS/DMEM, followed by stimulation with 100 ng/ml TNF-α. Cells after two hours from stimulation are washed with PBS(−) two times, and the following operation is performed to obtain an nucleus extract.

(i) Cells are recovered in 1 ml of an ice-cooled low osmotic pressure lysis buffer with a scraper. The buffer contains 10 mM of HEPES at pH 7.4, 10 mM of KCl, 1.5 mM of dithiothreitol, E-64-containing protease inhibitor cocktail, leupeptin, pepstatin A, bestatin, and aprotinin.

(ii) After 15 minutes, incubation is performed at an ice temperature, and 0.05% NP-40 is added. Thereafter, it is centrifuged at 1000 g at 4° C. for 1 minute.

(iii) Nucleus pellets are collected, and re-suspended in 100 μl of a high osmotic pressure extraction buffer. The buffer contains 20 mM of HEPES at pH 7.4, 0.4 mM of NaCl, 1 mM of EDTA, 1 mM of EGTA, 10% glycerol, 0.5 mM of dithiothreitol, E-64-containing protease inhibitor cocktail, leupeptin, pepstatin A, bestatin, and aprotinin.

(iv) After 15 minutes, incubation is performed at an ice temperature, and it is centrifuged at 1000 g at 4° C. for 1 minute.

(v) The supernatant is obtained as a nucleus extract, and an amount of a protein contained in the nucleus extract is quantified using a protein quantification kit. The nucleus extract is dispensed at a small scale, and is stored at −80° C. or lower.

<Preparation of Poly dI-dC copolymer>

A copolymer is added to the nucleus extract so that substances other than a target protein are not adhered to a double-stranded DNA 20. As a copolymer, Poly dI-dC (manufactured by Sigma, P-4929) is used. The copolymer is prepared as follows:

(i) A copolymer is suspended in a regeneration buffer to a concentration of 10 mg/ml, and the suspension is placed in a microcentrifuge tube having a volume of 1.5 ml. The regeneration buffer contains 50 mM of NaCl, 10 mM of Tris-HCl at pH 8.0, and 1 mM of EDTA at pH 8.0.

(ii) The copolymer is treated with ultrasound for 20 seconds at ultrasound setting 4, so as to obtain a uniform length of copolymer.

(iii) The copolymer is heated at 90° C. for 10 minutes, and is cooled to room temperature slowly.

(iv) Each 5 μl is dispensed, and is stored at −20° C.

(v) Before use, 45 μl of distilled water is added to adjust it to a concentration of 1 mg/ml.

[Experiment 3-1] Experiment of a reaction of a (fluorescently labeled) DNA having an AP-1-binding sequence and a cell nucleus extract. The Experiment was performed by stepwise changing a concentration of a cell nucleus extract.

The following solution shown in Table 19 is placed in a container, gently stirred with a tip of a chip, slightly tapped, and reacted at 34° C. for 1 hour. Then, FCS measurement is performed to obtain a translational diffusion time. FCS measurement was performed five times after each reaction under the condition of irradiation of laser light at a wavelength of 543 nm and an output of 100 μW for 15 seconds per one time.

TABLE 19

| | Concentration | Amount (total 20 μl) |
|---|---|---|
| Fluorescently Labeled double-stranded DNA 20 | | 2 μl |
| Cell nucleus extract | 0, 5, 10, 20, 30 or 40 μg of contained protein weight relative to total amount of 20 μl | Amount corresponding to 0, 5, 10, 20, 30 or 40 μg |
| Poly dI-dC | 1 mg/ml | Addition of 1 μg (=1 μl) relative to 10 μg of cell extract |
| dW | | Residual amount or suitable amount |
| 5 × binding buffer (for transcription factor AP-1) | | 4 μl |

In a reaction using 0 ng of a cell nucleus extract, a DNA-binding protein is not added, and thus a DNA-protein complex is not present, and a double-stranded DNA 20 remains unreacted. The product obtained after a reaction is a complex in which a DNA-binding protein contained in a cell nucleus extract is bound to a double-stranded DNA 20. Regarding an unreacted double-stranded DNA 20 and products obtained at each concentration of a cell nucleus extract, results of FCS measurement are shown in Table 20.

TABLE 20

Results of FCS measurement of DNA-AP-1 complex in Experiment 3-1

| Protein contained in cell nucleus extract [μg] | Difft. K1 [μs] | SD Difft. K1 | CPP [kHz] | CR [kHz] | SD Countrate [kHz] | n |
|---|---|---|---|---|---|---|
| 0 | 658.5 | 21.83 | 9.6 | 36.9 | 0.24 | 3.8 |
| 5 | 794 | 21.49 | 8.2 | 36.3 | 0.4 | 4.4 |
| 10 | 929.4 | 11.54 | 7.1 | 37 | 0.37 | 5.2 |
| 20 | 1052.6 | 139.7 | 7.4 | 38.2 | 0.95 | 5.1 |
| 30 | 1213.4 | 26.1 | 9.2 | 40.9 | 0.28 | 4.5 |
| 40 | 1113 | 61.05 | 11 | 42.3 | 0.44 | 3.8 |

As a concentration of a cell nucleus extract is increased, a translational diffusion time of the product is increased. Concentration dependency was recognized in a range of a concentration of a cell nucleus extract of up to 30 μg (see FIG. 12).

In addition, under the presumption that a transcription factor AP-1 is bound to a double-stranded DNA 20 in a c-Jun/c-Jun homodimer to form a DNA-protein complex, a translational diffusion time of a DNA-protein complex is obtained to be 1113.0 μs from a molecular weight of a DNA-protein complex, because a translational diffusion time is proportion to a cubic root of a molecular weight. In this experiment, a sum of an existence ratio of the reaction product having a translational diffusion of time of 1113.0 μs and an existence ratio of an unreacted double-stranded DNA 20 having a translational diffusion time of 658.5 μs is approximately 100%. Therefore, it can be said that the reaction product obtained in this experiment is a complex in which a transcription factor AP-1 in a cell nucleus extract is bound to a double-stranded DNA 20 (see FIG. 13).

[Experiment 3-2] Experiment of a reaction of a (fluorescently labeled) DNA having an NF-κB-binding sequence and a cell nucleus extract. The Experiment was performed by stepwise changing a concentration of a cell nucleus extract.

As a DNA, a double-stranded DNA 30 shown in FIG. 7 is used. The double-stranded DNA 30 consists of an oligo DNA 31 having a fluorescent label 4 (TAMRA label) at a 5'-terminal, and an oligo DNA 32 having a nucleic acid sequence complementary to that of the oligo DNA 31. The double-stranded DNA 30 has a GGGGCTTT sequence (a complementary sequence is a CCCCTGAAA sequence), which is a binding site 33 to which a transcription factor NF-κB binds.

The double-stranded DNA 30 is prepared in the same way as the double-stranded DNA 20, using 100 nM of a (fluorescently labeled) oligo DNA 31, and 100 nM of an oligo DNA 32 (see Example 2).

In this Experiment, a binding reaction experiment is performed in the same way as Experiment 3-1, using the following shown in Table 21, and the reaction product is measured by FCS to obtain a translational diffusion time.

TABLE 21

| | Concentration | Amount (total 20 μl) |
|---|---|---|
| Fluorescently labeled double-stranded DNA 30 | | 2 μl |
| Cell nucleus extract | 0, 5, 10, 20, 30 or 40 μg of contained protein weight relative to total amount of 20 μl | Amount corresponding to 0, 5, 10, 20, 30 or 40 μg |
| Poly dI-dC | 1 mg/ml | Addition of 1 μg (=1 μl) relative to 10 μg of cell extract |
| dW | | Residual amount or suitable amount |
| 5 × binding buffer (for transcription factor NF-κB) | | 4 μl |

TABLE 22

Composition of 5 × binding buffer (for transcription factor NF-κB)

| | Concentration | English name and others |
|---|---|---|
| Tris-HCl pH 7.5 | 50 mM | Tris-HCl |
| Potassium chloride | 250 mM | KCl |
| EDTA | 1 mM | Ethylenediaminetetraacetic acid |
| DTT | 2.5 mM | Dichlorodiphenyltrichloroethane |
| Glycerol | 10% concentration | Glycerol |

As in the case of Experiment 3-1, a DNA-binding protein is not added in a reaction using a cell nucleus extract having a concentration of 0 μg, and thus a DNA-protein complex is not present, and a double-stranded DNA 30 remains unreacted. The product after the reaction is a complex in which a DNA-binding protein contained in a cell nucleus extract is bound to a double-stranded DNA 30. Regarding an unreacted double-stranded DNA 30 and the products obtained at each concentration of a cell nucleus extract, results of FCS measurement are shown in Table 23.

TABLE 23

Results of FCS measurement of DNA-NF-κB complex in Experiment 3-2

| Protein contained in cell nucleus extract [μg] | Difft. K1 [μs] | SD Difft. K1 | CPP [kHz] | CR [kHz] | SD Countrate [kHz] | n |
|---|---|---|---|---|---|---|
| 0 | 568.7 | 16.87 | 24.9 | 48.1 | 0.53 | 1.9 |
| 5 | 815.7 | 26.96 | 24.3 | 52 | 0.95 | 2.1 |
| 10 | 964.4 | 35.48 | 21 | 53.8 | 0.95 | 2.6 |
| 20 | 1327.7 | 59.23 | 17.9 | 47.3 | 0.71 | 2.6 |
| 30 | 1468.7 | 70.69 | 17 | 47.3 | 0.74 | 2.8 |
| 40 | 1355.7 | 39.14 | 15.9 | 42.5 | 0.28 | 2.7 |

Also in the present experiment as well as in Experiment 3-1, as a concentration of a cell nucleus extract is increased, a translational diffusion time of the product is extended. A translational diffusion time is maximum at 30 μg of a concentration of a cell nucleus extract, and concentration dependency was recognized (see FIG. 14).

Figure 15:
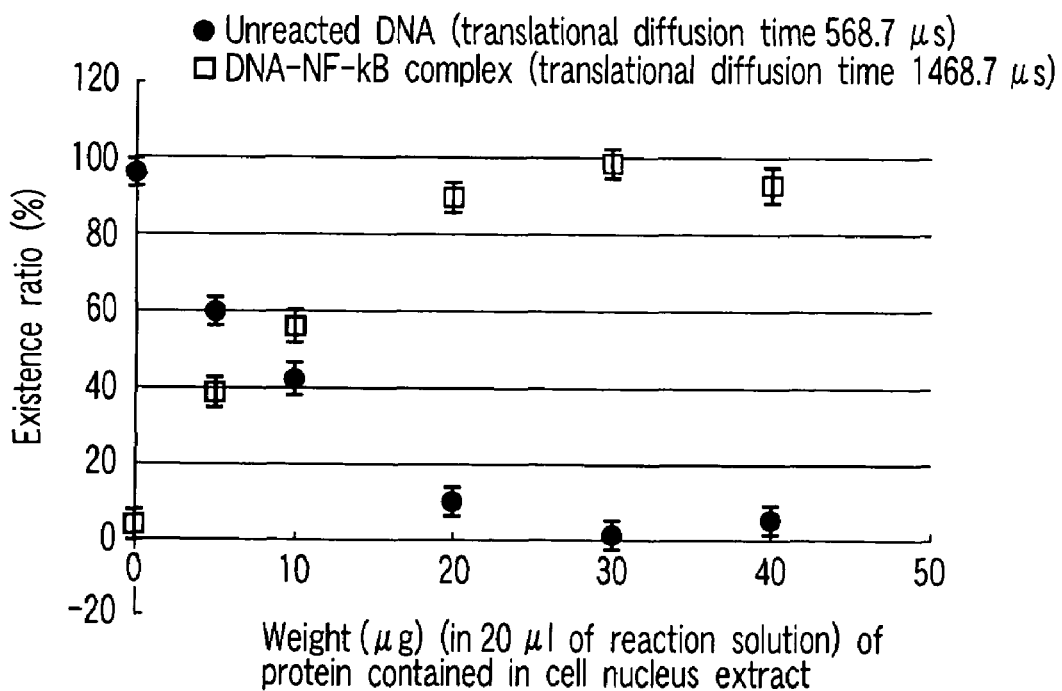
FIG. 15 is a graph showing an existence ratio of an unreacted product (unreacted DNA) and a product (DNA-NF-κB complex) relative to a concentration of a cell nucleus extract in Experiment 3-2.

In addition, under the presumption that the reaction product is a product obtained by binding a double-stranded DNA 30 and a transcription factor NF-κB, and that binding by *p50/p50 and binding by p50/p65 are averagely present, a translational diffusion time of the reaction product is 1468.7 μs. An existence ratio of the reaction product having a translational diffusion time of 1468.7 μs and an existence ratio of an unreacted double-stranded DNA 30 having a translational diffusion time of 568.7 μs are shown in FIG. 15. A sum of respective existence ratios is approximately 100%. Therefore, it can be said that the reaction product obtained in this experiment is a complex in which a transcription factor NF-κB in a cell nucleus extract is bound to a double-stranded DNA 30.

In the case of detecting whether or not a transcription factor is contained in a cell nucleus extract, as explained in Example 2, the presence of a transcription factor can be detected, by stepwise adding a cell nucleus extract to a solution containing a fluorescently labeled double-stranded DNA having a binding site to which a transcription factor binds, and measuring the product by FCS to obtain a translational diffusion time. In addition, an approximate existence ratio of a DNA-protein complex and an unreacted double-stranded DNA can be detected from the result of FCS measurement, and a molecular weight of a DNA-protein complex and a molecular weight of an unreacted double-stranded DNA.

In the case of detecting whether or not a transcription factor AP-1 is contained in a cell nucleus extract, a fluorescently labeled double-stranded DNA 20 having a binding site 26 to which a transcription factor AP-1 binds is used as a double-stranded DNA. In the case of detecting whether or not a transcription factor NF-κB is contained in a cell nucleus extract, a fluorescently labeled double-stranded DNA 30 having a binding site 33 to which a transcription factor NF-κB binds is used as a double-stranded DNA. It can be said that a transcription factor is contained in a cell nucleus extract, if the following results is obtained: as an addition amount of a cell nucleus extract is increased, a translational diffusion time is extended, and after a maximum value is taken, a translational diffusion time is decreased.

Example 4

In the present Example, a binding reaction of a DNA and a transcription factor AP-1 in a cell nucleus extract is detected by performing competitive assay in which a competitive DNA is added.

[Experiment 4-1] Experiment of a reaction of a (fluorescently labeled) DNA having an AP-1-binding sequence and a cell nucleus extract, when an (unlabeled) double-stranded DNA having an AP-1-binding sequence is added. The Experiment was performed by stepwise changing a concentration of the (unlabeled) double-stranded DNA.

As the (unlabeled) double-stranded DNA to be added, a double-stranded DNA 24 which has the same sequence as that of the double-stranded DNA 20 but has not been fluorescently labeled is used. A concentration of a cell nucleus extract is set to be 30 μg at which a binding reaction was sufficiently generated in Experiment 3-1.

The following solution shown in Table 24 is placed in a container, gently stirred with a tip of a chip, slightly tapped, and reacted at 34° C. for 1 hour. Then, FCS measurement is performed to obtain a translational diffusion time. FCS measurement was performed five times after each reaction under the condition of irradiation of laser light at a wavelength of 543 nm and an output of 100 µW for 15 seconds per one time.

TABLE 24

|  | Concentration | Amount (total 20 µl) |
|---|---|---|
| Fluorescently labeled double-stranded DNA 20 |  | 2 µl |
| Cell nucleus extract (when cell nucleus extract is not added, only extractant for cell nucleus is added) | 30 µg relative to total amount of 20 µl | Amount corresponding to 30 µg |
| Poly dI-dC | 1 mg/ml | 3 µl |
| Unlabeled double-stranded DNA 24 diluted with dW | 0, 10, 25, 50, 100, 200 or 400 ng relative to total amount of 20 µl | 6.7 µl |
| 5 × binding buffer (for transcription factor AP-1) |  | 4 µl |

[Experiment 4-2] Experiment of a reaction of a (fluorescently labeled) DNA having an AP-1-binding sequence and a cell nucleus extract, when an (unlabeled) double-stranded DNA having a sequence which is slightly different from an AP-1-binding sequence is added. The Experiment was performed by stepwise changing a concentration of the (unlabeled) double-stranded DNA.

As the (unlabeled) double-stranded DNA to be added, a double-stranded DNA 25 having a sequence, a part of which is different from a double-stranded DNA 20, and which has not been fluorescently labeled is used. The double-stranded DNA 25 is different from a double-stranded DNA 20 in a part of a binding site 26 by only two bases (see FIG. 6). Experiment 4-2 was performed using the double-stranded DNA 25 in the same way as Experiment 4-1.

[Experiment 4-3] Experiment of a reaction of a (fluorescently labeled) DNA having an AP-1-binding sequence and a cell nucleus extract, when an (unlabeled) double-stranded DNA having no AP-1-binding sequence is added. The Experiment was performed by stepwise changing a concentration of the (unlabeled) double-stranded DNA.

As the (unlabeled) double-stranded DNA to be added, an unlabeled double-stranded DNA 18 having an *Escherichia coli*-derived double-stranded random sequence having no AP-1-binding sequence is used. Experiment 4-3 was performed using the double-stranded DNA 18 in the same way as Experiment 4-1.

Figure 16:
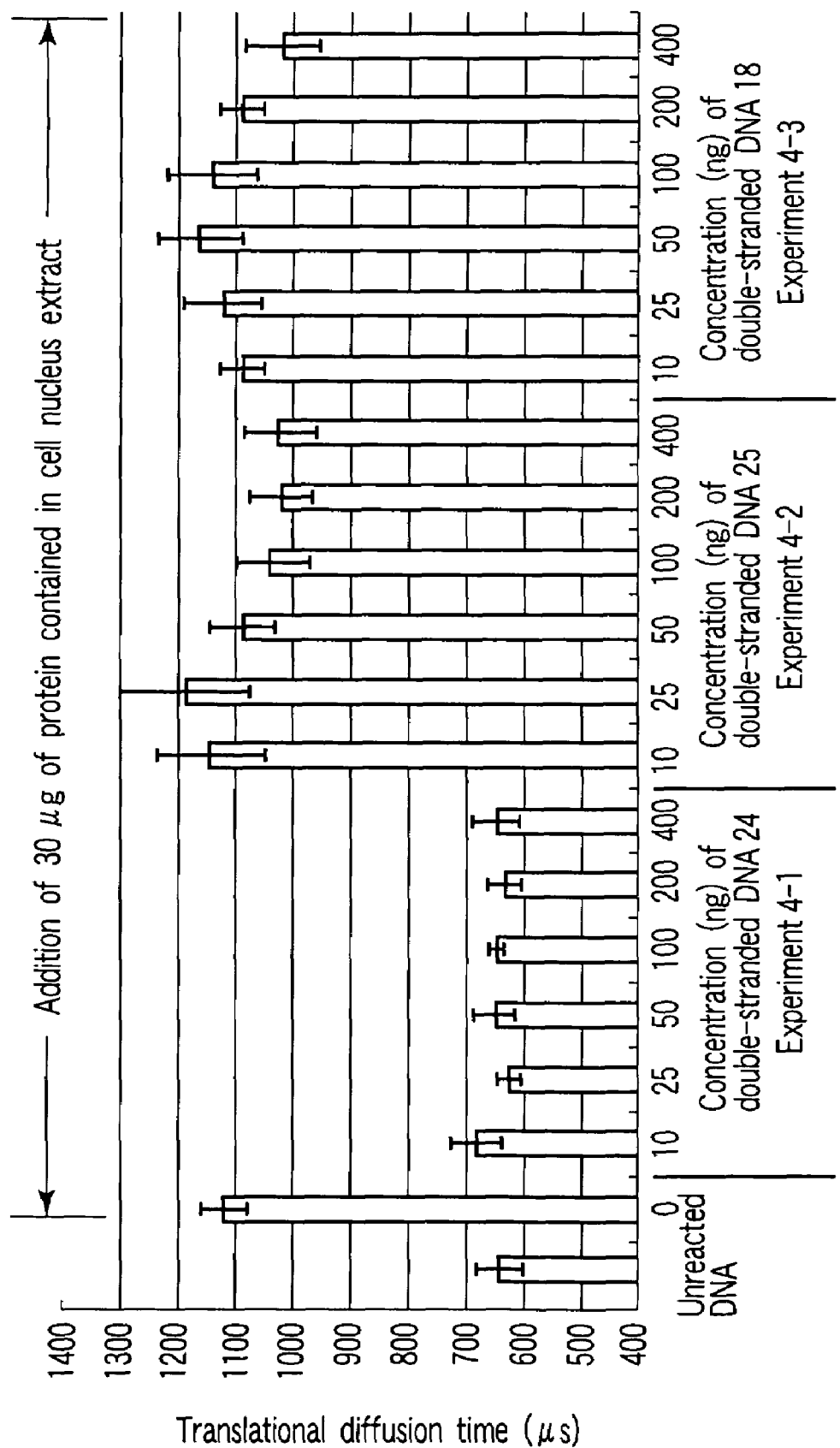
FIG. 16 is a graph showing a translational diffusion time of a product (DNA-protein complex) relative to a concentration of (unlabeled) each double-stranded DNA in Experiments 4-1 to 4-3.

Results of Experiments 4-1 to 4-3 are shown in FIG. 16. From the results of Experiment 4-1, a translational diffusion time of the product which can be confirmed by a fluorescent label (that is, a DNA-protein complex obtained by binding of a double-stranded DNA 20 and a DNA-binding protein in a cell nucleus extract) was not greatly extended, as compared with a translational diffusion time of an unreacted double-stranded DNA 20. Therefore, it was confirmed that binding of a double-stranded DNA 20 and a transcription factor AP-1 5 in a cell nucleus extract is inhibited by adding a double-stranded DNA 24.

In addition, from the results of Experiment 4-2, a translational diffusion time of the binding product of a double-stranded DNA 20 and a cell nucleus extract is approximately the same between the case where a double-stranded DNA 25 is added and the case where such competitive DNA 25 is not added. Therefore, regarding a reaction of a double-stranded DNA 20 and a transcription factor AP-1 5 in a cell nucleus extract, binding inhibition was not recognized by adding a double-stranded DNA 25 having a sequence which is different from that of a double-stranded DNA 20 by only two bases.

In addition, from the results of Experiment 4-3, a translational diffusion time of the binding product of a double-stranded DNA 20 and a cell nucleus extract is approximately the same between the case where a double-stranded DNA 18 is added and the case where such competitive DNA 18 is not added. Therefore, regarding a reaction of a double-stranded DNA 20 and a transcription factor AP-1 5 in a cell nucleus extract, binding inhibition was not recognized by adding a double-stranded DNA 18.

From the results of competition assay performed in the above Experiments 4-1 to 4-3, it was demonstrated that a transcription factor AP-1 in a cell nucleus extract binds to a specific sequence of a DNA contained in a cell nucleus extract.

Example 5

In the present Example, a binding reaction of a DNA and a transcription factor NF-κB in a cell nucleus extract is detected by performing competition assay in which a competitive DNA is added.

[Experiment 5-1] Experiment of a reaction of a (fluorescently labeled) DNA having an NF-κB-binding sequence and a cell nucleus extract, when an (unlabeled) double-stranded DNA having an NF-κB-binding sequence is added. The Experiment was performed by stepwise changing a concentration of the (unlabeled) double-stranded DNA.

As the (unlabeled) double-stranded DNA to be added, a double-stranded DNA 34 which has the same sequence as that of a double-stranded DNA 30 but has not been fluorescently labeled is used. A concentration of a cell nucleus extract is set to be 30 µg at which a binding reaction was sufficiently generated in Experiment 3-1.

The following solution shown in Table 25 is placed in a container, gently stirred with a tip of a chip, slightly tapped, and reacted at 34° C. for 1 hour. Then, FCS measurement is performed to obtain a translational diffusion time. FCS measurement was performed five times after each reaction under the condition of irradiation of laser light at a wavelength of 543 nm and an output of 100 µW for 15 seconds per one time.

TABLE 25

|  | Concentration | Amount (total 20 µl) |
|---|---|---|
| Fluorescently labeled double-stranded DNA 30 |  | 2 µl |
| Cell nucleus extract (when cell nucleus extract is not added, only extractant for cell nucleus is added) | 30 µg is added relative to total amount of 20 µl | Amount corresponding to 30 µg |

TABLE 25-continued

|  | Concentration | Amount (total 20 μl) |
|---|---|---|
| Poly dI-dC | 1 mg/ml | 3 μl |
| Unlabeled competitive double-stranded DNA 34 diluted with dW | 0, 10, 25, 50, 100, 200 or 400 ng relative to total amount of 20 μl | 6.7 μl |
| 5 × binding buffer (for transcription factor NF-κB) |  | 4 μl |

[Experiment 5-2] Experiment of a reaction of a (fluorescently labeled) DNA having an NF-κB-binding sequence and a cell nucleus extract, when an (unlabeled) double-stranded DNA having a sequence which is slightly different from an NF-κB-binding sequence is added. The Experiment was performed by stepwise changing a concentration of the (unlabeled) double-stranded DNA.

As the (unlabeled) double-stranded DNA to be added, a double-stranded DNA 35 which has a sequence, a part of which is different from a double-stranded DNA 30, and which has not been fluorescently labeled is used. The double-stranded DNA 35 is different from a double-stranded DNA 30 in a part of a binding site 33 by only one base (see FIG. 7). Experiment 5-2 was performed using the double-stranded DNA 35 in the same way as Experiment 5-1.

[Experiment 5-3] Experiment of a reaction of a (fluorescently labeled) DNA having an NF-κB-binding sequence and a cell nucleus extract, when an (unlabeled) double-stranded DNA having no NF-κB-binding sequence is added. The Experiment was performed by stepwise changing a concentration of the (unlabeled) double-stranded DNA.

As the (unlabeled) double-stranded DNA to be added, a double-stranded DNA 18 which has an *Escherichia coli*-derived double-stranded random sequence having no NF-κB-binding sequence and which has not been fluorescently labeled is used. Experiment 5-3 was performed using the double-stranded DNA 18 in the same way as Experiment 5-1.

FIG. 17 shows results of Experiments 5-1 to 5-3. From the results of Experiment 5-1, a translational diffusion time of the product which can be confirmed by a fluorescent label (that is, a DNA-protein complex obtained by binding of a double-stranded DNA 30 and a DNA-binding protein in a cell nucleus extract) was not greatly extended, as compared with a translational diffusion time of an unreacted double-stranded DNA 30.

Therefore, it was confirmed that binding of a double-stranded DNA 30 and a transcription factor AP-1 5 in a cell nucleus extract is inhibited by adding a competitive double-stranded DNA 34.

In addition, from the results of Experiment 5-2, a translational diffusion time of the binding product of a double-stranded DNA 30 and a cell nucleus extract is approximately the same between the case where a double-stranded DNA 35 is added and the case where nothing is added. Therefore, regarding a reaction of a double-stranded DNA 35 and a transcription factor NF-κB in a cell nucleus extract, binding inhibition was not recognized by adding a double-stranded DNA 35 having a sequence different from that of a double-stranded DNA 30 by only one base.

In addition, from the results of Experiment 5-3, a translational diffusion time of the binding product of a double-stranded DNA 30 and a cell nucleus extract is approximately the same between the case where a double-stranded DNA 18 is added and the case where such competitive DNA 18 is not added. Therefore, regarding a reaction of a double-stranded DNA 30 and a transcription factor NF-κB in a cell nucleus extract, binding inhibition was not recognized by adding a double stranded DNA 18.

From the results of competition assay performed in the above Experiments 5-1 to 5-3, it was demonstrated that a transcription factor NF-κB in a cell nucleus extract binds to a specific sequence of a DNA contained in a cell nucleus extract.

Example 6

In the present Example, regarding activation of a transcription factor in a cell nucleus, dependency on stimulation with a tumor necrosis factor TNF-α at the time of extraction of cell nucleus is examined. Specifically, HeLa cell is stimulated using a tumor necrosis factor TNF-α, and a degree of activation of a transcription factor AP-1 and a transcription factor NF-κB in a cell nucleus is detected with the lapse of time. It is known that a transcription factor AP-1 and a transcription factor NF-κB have activity to an extent in a nucleus of HeLa cell, even when the cell is not stimulated with PMA (phorbol 12-myristate 13-acetate), cytokine or the like.

[Experiment 6-1] Experiment of a reaction of a (fluorescently labeled) DNA having an AP-1-binding sequence and a cell nucleus extract. The Experiment was performed using a cell nucleus extract which is extracted under the condition of a different time length of stimulation with a tumor necrosis factor TNF-α.

50 ng/ml of a tumor necrosis factor TNF-α was added to HeLa cell, and the HeLa cell was stimulated for 0, 15, 30, 60, 120 or 180 minutes. Then, a nucleus extract was prepared from each HeLa cell (for preparation method, see Example 3). A concentration of a nucleus extract was set to be 20 μg.

The following shown in Table 26 are used to perform a binding reaction experiment in the same way as Experiment 3-1.

TABLE 26

|  | Concentration | Amount (total 20 μl) |
|---|---|---|
| Fluorescently labeled double-stranded DNA 20 |  | 2 μl |
| Cell nucleus extract (which is prepared under the condition of 0, 15, 30, 60, 120 or 180 minutes of a time length of stimulation with tumor necrosis factor TNF-α) | 20 μg relative to total amount of 20 μl | Amount corresponding to 20 μg |
| Poly dI-dC | 1 mg/ml | 2 μl |
| dW |  | Residual amount |
| 5 × binding buffer (for transcription factor AP-1) |  | 4 μl |

Figure 18:
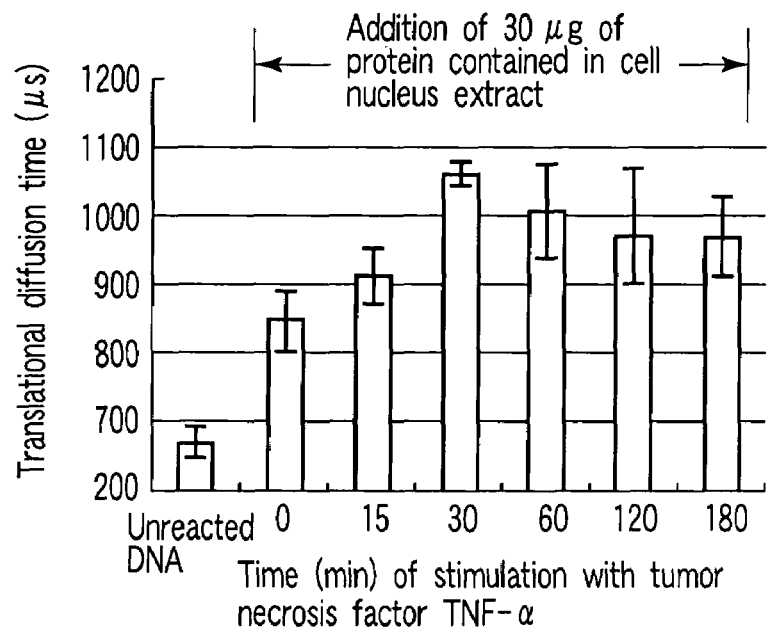
FIG. 18 is a graph showing a translational diffusion time of a product (DNA-AP-1 complex) relative to a stimulation time in Experiment 6-1.

FIG. 18 shows a translational diffusion time of the product relative to a stimulation time. A translational diffusion time of the binding reaction product of a (labeled) double-stranded DNA 20 and a cell nucleus extract which has been stimulated with a tumor necrosis factor TNF-α for 30 minutes is greatest. The greatest value is approximately the same as a translational diffusion time of the reaction product obtained when a concentration of a nucleus extract is set to be 20 μg in Experiment 3-1. Therefore, it can be said that a transcription factor AP-1 in a cell nucleus extract is sufficiently activated by a stimulation time of 30 minutes.

[Experiment 6-2] Experiment of a reaction of a (fluorescently labeled) DNA having an NF-κB-binding sequence and a cell nucleus extract. The Experiment was performed using a cell nucleus extract which is extracted under the condition of a different time length of stimulation with a tumor necrosis factor TNF-α.

In the same way as Experiment 6-1, 50 ng/ml of a tumor necrosis factor TNF-α was added to HeLa cell, and the HeLa cell was stimulated for 0, 15, 30, 60, 120 or 180 minutes. Then, a nucleus extract was prepared from each HeLa cell.

The following shown in Table 27 are used to perform a binding reaction experiment in the same way as Experiment 3-2.

TABLE 27

|  | Concentration | Amount (total 20 μl) |
|---|---|---|
| Fluorescently labeled double-stranded DNA 30 |  | 2 μl |
| Cell nucleus extract (which is prepared under the condition of 0, 15, 30, 60, 120 or 180 minutes of a time length of stimulation with tumor necrosis factor TNF-α) | 20 μg relative to total amount of 20 μl | Amount corresponding to 20 μg |
| Poly dI-dC | 1 mg/ml | 2 μl |
| dW |  | Residual amount |
| 5 × binding buffer (for transcription factor NF-κB) |  | 4 μl |

Figure 19:
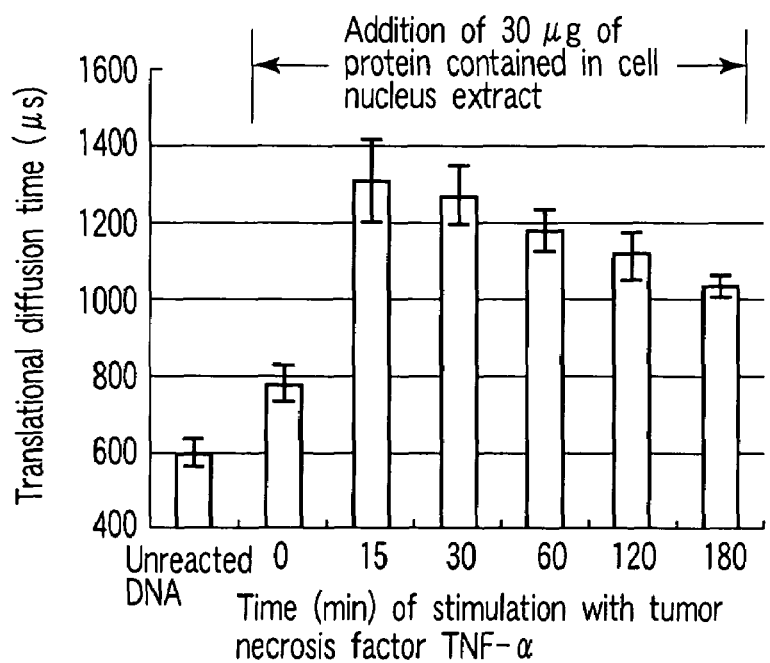
FIG. 19 is a graph showing a translational diffusion time of a product (DNA-NF-κB complex) relative to a stimulation time in Experiment 6-2.

FIG. 19 shows a translational diffusion time of the product relative to a stimulation time. A translational diffusion time of the binding reaction product of a (labeled) double-stranded DNA 30 and a cell nucleus extract which has been stimulated with a tumor necrosis factor TNF-α for 15 minutes is greatest. The greatest value is approximately the same as a translational diffusion time of the reaction product obtained when a concentration of a nucleus extract is set to be 20 μg in Experiment 3-2. Therefore, it can be said that a transcription factor NF-κB in a cell nucleus extract was sufficiently activated by a stimulation time of 15 minutes.

In the case of detecting whether or not a transcription factor AP-1 is contained in a cell nucleus extract, the presence of a transcription factor can be detected by adding 50 ng/ml of a tumor necrosis factor TNF-α to a cell to stimulate the cell for 30 minutes; extracting a cell nucleus from the cell; reacting the cell nucleus extract with a double-stranded DNA 20; and performing FCS measurement to obtain a translational diffusion time. In addition, in the case of detecting whether or not a transcription factor NF-κB is contained in a cell nucleus extract, 50 ng/ml of a tumor necrosis factor TNF-α is preferably added to a cell to stimulate the cell for 15 minutes.

Example 7

In the present Example, regarding activation of a transcription factor in a cell nucleus, dependency on stimulation with APDC (Ammonium pyrrolidinedithiocarbamate) and a tumor necrosis factor TNF-α at the time of extraction of cell nucleus is examined. Specifically, HeLa cell is stimulated using APDC and a tumor necrosis factor TNF-α, and a degree of activation of a transcription factor AP-1 and a transcription factor NF-κB in a cell nucleus is detected. It is said that APDC promotes activation of a transcription factor AP-1 and, on the other hand, suppresses activation of a transcription factor NF-κB.

Two hours after addition of APDC, a tumor necrosis factor TNF-α is added to stimulate HeLa cell for 30 minutes, from which a nucleus extract is prepared. A nucleus extract having a concentration of 5, 10 or 20 μg is prepared. Stimulation on a cell is performed in the following two cases.

(I) The case where stimulation with only a tumor necrosis factor TNF-α is performed for 30 minutes. A concentration of a tumor necrosis factor TNF-α is 0, 10, 25 or 50 ng/ml.

(II) The case where stimulation with a tumor necrosis factor TNF-α is performed for 30 minutes, two hours after addition of APDC. A concentration of APDC is 10, 100 or 200 μM relative to a 50 ng/ml of a tumor necrosis factor TNF-α.

[Experiment 7-1] Experiment of a reaction of a (fluorescently labeled) DNA having an AP-1-binding sequence and a cell nucleus extract. The Experiment was performed using a cell nucleus extract which is extracted under the condition of a different concentration of an added tumor necrosis factor TNF-α and a different concentration of an added APDC.

The following shown in Table 28 are used to perform a binding reaction experiment in the same way as Experiment 3-1.

TABLE 28

|  | Concentration | Amount (total 20 μl) |
|---|---|---|
| Fluorescently labeled double-stranded DNA 20 |  | 2 μl |
| Cell nucleus extract | 5, 10 or 20 μg of an extract from a cell stimulated by (i) or 5, 10 or 20 μg of an extract from a cell stimulated by (ii), relative to total amount of 20 μl | Amount corresponding to 5, 10 or 20 μg (when an amount does not attain 20 μg, an equivalent amount of an extractant for a cell is added) |
| Poly dI-dC | 1 mg/ml | Addition of 1 μg (=1 μl) relative to 10 μg of cell extract |
| dW |  | Residual amount |
| 5 × binding buffer (for transcription factor AP-1) |  | 4 μl |

FIG. 20 shows a translational diffusion time of the product relative to each stimulation condition. Stimulation dependency of a translational diffusion time of the product was seen depending on a concentration of a tumor necrosis factor TNF-α and a concentration of APDC. In particular, when both of stimulation with APDC and stimulation with a tumor necrosis factor TNF-α are performed, and a concentration of APDC is 100 μM and 200 μM relative to 50 ng/ml of a tumor necrosis factor TNF-α, a translational diffusion time of the product is great. Therefore, it can be said that a transcription factor AP-1 in a cell nucleus extract is most activated at a combination of these concentrations.

[Experiment 7-2] Experiment of a reaction of a (fluorescently labeled) DNA having an NH-κB-binding sequence and a cell nucleus extract. The Experiment was performed using a cell nucleus extract which is extracted under the condition of a different concentration of an added tumor necrosis factor TNF-α and a different concentration of added APDC.

The following shown in Table 29 are used to perform a binding reaction experiment in the same way as Experiment 3-2.

TABLE 29

|  | Concentration | Amount (total 20 μl) |
|---|---|---|
| Fluorescently labeled double-stranded DNA 30 |  | 2 μl |
| Cell nucleus extract | 5, 10 or 20 μg of an extract from a cell stimulated by (i), or 5, 10 or 20 μg of an extract from a cell stimulated by (ii), relative to total amount of 20 μl | Amount corresponding to 5, 10 or 20 μg (when an amount does not attain 20 μg, an equivalent amount of an extractant for a cell is added) |
| Poly dI-dC | 1 mg/ml | Addition of 1 μg (=1 μl) relative to 10 μg of cell extract |
| dW |  | Residual amount |
| 5 × binding buffer (for transcription factor NF-κB) |  | 4 μl |

FIG. 21 shows a translational diffusion time of the product relative to each stimulating condition. Stimulation dependency of a translational diffusion time of the product was seen depending on a concentration of a tumor necrosis factor TNF-α and a concentration of APDC. In particular, when stimulation with only a tumor necrosis factor TNF-α is performed, and a concentration of a tumor necrosis factor TNF-α is 50 ng/ml, a translational diffusion time of the product is great. Therefore, it can be said that a transcription factor NF-κB in a cell nucleus extract is most activated at the concentration.

From the results of Experiments 7-1 and 7-2, it was demonstrated that APDC promotes activation of a transcription factor AP-1 by a tumor necrosis factor TNF-α, and suppresses activation of a transcription factor NF-κB by a tumor necrosis factor TNF-α.

In the case of detecting whether or not a transcription factor AP-1 is contained in a cell nucleus extract, the presence of a transcription factor can be detected by adding a tumor necrosis factor TNF-α to a cell to stimulate the cell for 30 minutes, two hours after addition of APDC; extracting a cell nucleus from the cell; reacting the cell nucleus extract with a double-stranded DNA 20; and performing FCS measurement to obtain a translational diffusion time. A concentration of APDC is preferably not lower than 100 μM and not higher than 200 μM, relative to 50 ng/ml of a tumor necrosis factor TNF-α.

In addition, in the case of detecting whether or not a transcription factor NF-κB is contained in a cell nucleus extract, a transcription factor NF-κB can be detected precisely, by comparing a translational diffusion time obtained when stimulation is performed with only a tumor necrosis factor TNF-α and a translational diffusion time obtained when stimulation is performed with both APDC and a tumor necrosis factor TNF-α. If a translational diffusion time obtained when stimulation is performed with only a tumor necrosis factor TNF-α is greater than the other translational diffusion time, it can be said that a transcription factor NF-κB is contained in a cell nucleus extract.

As shown in the aforementioned respective Examples, information for obtaining a translational diffusion time is obtained by mixing of a sample and measurement by fluorescence correlation spectroscopy (FCS). As a result, result of detection can be obtained simply and in a short time without performing troublesome operation such as utilization of a radioisotope and selection by an electrophoresis method or immobilization of a molecule on a solid substrate. Further, even when a crude sample such as an unpurified cell nucleus extract is used, a DNA-protein complex of a double-stranded DNA and a transcription factor can be detected precisely. Further, even in the presence of a double-stranded DNA which is different, by only 1 base or 2 bases, from an inherent double-stranded DNA to which a transcription factor inherently binds, a DNA-protein complex resulting from the inherent double-stranded DNA and a transcription factor can be detected without preventing a binding reaction between them. Therefore, the measuring method by FCS according to the present invention is useful for detecting a particular DNA-binding protein (such as transcription factor or intranuclear receptor) present in a crude sample such as a cell nucleus extract. In addition, the effect of stimulation with a cytokine on a time-dependent amount of expression of a transcription factor or the effect of APDC can be also detected precisely.

In the aforementioned respective Examples, fluorescent correlation spectroscopy (FCS) was used in order to obtain a translational diffusion time of the product, but Fluorescence Intensity Multiple Distribution Analysis may be used instead of the fluorescence correlation spectroscopy (FCS).

What is claimed is:

1. A method of detecting a transcription factor NF-κB in a cell nucleus extract, comprising: adding a tumor necrosis factor TNF-α to a cell, and then extracting a cell nucleus from the cell; mixing the extracted cell nucleus with a solution containing a fluorescently labeled double-stranded DNA comprising a transcription factor NF-κB-binding sequence; and obtaining a translational diffusion time of a substance having a fluorescent label in the mixed solution by fluorescence correlation spectroscopy.

2. A method of detecting a transcription factor NF-κB in a cell nucleus extract, comprising:

obtaining an extracted cell nucleus by adding a tumor necrosis factor TNF-α to a cell, extracting a cell nucleus from the cell, and performing a first mixing step of mixing said extracted cell nucleus with a solution containing a fluorescently labeled double-stranded DNA comprising a transcription factor NF-κB-binding sequence;

obtaining an extracted cell nucleus by adding APDC and then a tumor necrosis factor TNF-α to a cell, extracting a cell nucleus from the cell, and performing a second mixing step of mixing said extracted cell nucleus with a solution containing a fluorescently labeled double-stranded DNA comprising a transcription factor NF-κB binding sequence;

performing a first calculating step of obtaining a translational diffusion time of a substance having a fluorescent label in the mixed solution obtained in the first mixing step by fluorescence correlation spectroscopy;

performing a second calculating step of obtaining a translational diffusion time of a substance having a fluorescent label in the mixed solution obtained in the second mixing step by fluorescence correlation spectroscopy; and performing a step of comparing the translational diffusion time obtained in the first calculating step and the translational diffusion time obtained in the second calculating step.

3. The method according to claim 1, wherein the particle number of the fluorescently labeled double-stranded DNA in a confocal volume of the fluorescence correlation spectroscopy is 2 to 5.

4. The method according to claim 2, wherein the particle number of the fluorescently labeled double-stranded DNA in a confocal volume of the fluorescence correlation spectroscopy is 2 to 5.

* * * * *